(12) United States Patent
Chessari et al.

(10) Patent No.: US 7,629,356 B2
(45) Date of Patent: Dec. 8, 2009

(54) SUBSTITUTED PYRROLO[3,4-B]PYRIDINAMINES AND PHARMACEUTICAL COMPOSITIONS

(75) Inventors: Gianni Chessari, Cambridge (GB); Miles Stuart Congreve, Cambridge (GB); Jörg Holenz, Södertälje (SE); Christopher Murray, Cambridge (GB); Sahil Patel, Cambridge (GB); Laszlo Rakos, Södertälje (SE); Didier Rotticci, Södertälje (SE)

(73) Assignees: AstraZeneca AB, Sodertalje (SE); Astex Therapeutics, Cambridge (GB)

( * ) Notice: Subject to any disclaimer, the term of this patent is extended or adjusted under 35 U.S.C. 154(b) by 0 days.

(21) Appl. No.: 12/120,736

(22) Filed: May 15, 2008

(65) Prior Publication Data

US 2009/0233945 A9    Sep. 17, 2009

Related U.S. Application Data

(60) Provisional application No. 60/948,007, filed on Jul. 5, 2007, provisional application No. 60/938,005, filed on May 15, 2007.

(51) Int. Cl.
*A01N 43/42* (2006.01)

(52) U.S. Cl. ................... 514/300; 546/276.7
(58) Field of Classification Search ............... 514/300; 546/276.7
See application file for complete search history.

(56) References Cited

U.S. PATENT DOCUMENTS

| | | | |
|---|---|---|---|
| 2006/0281729 | A1 | 12/2006 | Iserloh et al. |
| 2007/0049589 | A1 | 3/2007 | Thompson, III et al. |
| 2007/0099875 | A1 | 5/2007 | Zhu et al. |
| 2007/0099898 | A1 | 5/2007 | Zhu et al. |

FOREIGN PATENT DOCUMENTS

| | | | |
|---|---|---|---|
| EP | 686673 | A1 | 6/1995 |
| EP | 742217 | A1 | 5/1996 |
| WO | 99/11643 | A1 | 3/1999 |
| WO | 2006/020879 | | 2/2006 |
| WO | 2006/076284 | A2 | 7/2006 |
| WO | 2006/099379 | A2 | 9/2006 |
| WO | 2006/138217 | A1 | 12/2006 |
| WO | 2006/138264 | A2 | 12/2006 |
| WO | 2006/138265 | A2 | 12/2006 |
| WO | 2006/138266 | A2 | 12/2006 |
| WO | 2007/011810 | A1 | 1/2007 |
| WO | 2007/049532 | A1 | 5/2007 |
| WO | 2007/058602 | A2 | 5/2007 |
| WO | 2007/146225 | A2 | 12/2007 |
| WO | 2007/149033 | A1 | 12/2007 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, p. 18.*
Blanchard, Barbara; PNAS, Oct. 2004, 101 (40), 14326-14332.
Barrett, P et al, J. Chem. Soc., 1939, 1809-20.
Bartlett, R et al, J. Chem. Soc. Section C., 1969, 1, 129-33.
Sawanishi et al, Chemical & Pharmaceutical Bulletin, 1985, 33 (10), 4564-71.
Siling, S et al, Doklady Akademii Nauk SSSR, 1988, 299 (3), 633-5.
De Strooper, Bart et al., A Firm Base for Drug Development, Dec. 1999, Nature 402, 1999, 471-472.
Yankner B A., New Clues to Alzheimer's Disease: Unraveling the Roles of Amyloid and Tau, Nature Medicine, 1996, 2(8), 850-852.
Von Angerer, S. "Product class 12: pyrimidines", Science of Synthesis, 2004, 16, 379-572.

\* cited by examiner

*Primary Examiner*—James O Wilson
*Assistant Examiner*—Douglas M Willis
(74) *Attorney, Agent, or Firm*—David M. Gryte

(57) ABSTRACT

This invention relates to substituted pyrrolo[3,4-b]pyridinamines having the structural formula IA below:

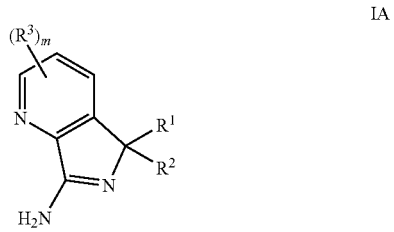

and to their pharmaceutically acceptable salt, compositions and methods of use. These novel compounds provide a treatment or prophylaxis of cognitive impairment, Alzheimer Disease, neurodegeneration and dementia.

19 Claims, No Drawings

SUBSTITUTED PYRROLO[3,4-B]PYRIDINAMINES AND PHARMACEUTICAL COMPOSITIONS

CROSS-REFERENCE TO RELATED APPLICATIONS

This application claims priority to U.S. provisional Ser. No. 60/948,007 filed Jul. 5, 2007, and to U.S. provisional Ser. No. 60/938,005 filed May 15, 2007, each of which is incorporated herein by reference in its entirety.

BACKGROUND OF THE INVENTION (1) Field of the Invention

The present invention relates to novel compounds, their pharmaceutical compositions. In addition, the present invention relates to therapeutic methods for the treatment and/or prevention of Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration.

(2) Description of Related Art

Several groups have identified and isolated aspartate proteinases that have β-secretase activity (Hussain et al., 1999; Lin et. al, 2000; Yan et. al, 1999; Sinha et. al., 1999 and Vassar et. al., 1999). β-secretase is also known in the literature as Asp2 (Yan et. al, 1999), Beta site APP Cleaving Enzyme (BACE) (Vassar et. al., 1999) or memapsin-2 (Lin et al., 2000). BACE was identified using a number of experimental approaches such as EST database analysis (Hussain et al. 1999); expression cloning (Vassar et al. 1999); identification of human homologs from public databases of predicted $C.$ $elegans$ proteins (Yan et al. 1999) and finally utilizing an inhibitor to purify the protein from human brain (Sinha et al. 1999). Thus, five groups employing three different experimental approaches led to the identification of the same enzyme, making a strong case that BACE is a β-secretase. Mention is also made of the patent literature: WO96/40885, EP871720, U.S. Pat. Nos. 5,942,400 and 5,744,346, EP855444, U.S. Pat. No. 6,319,689, WO99/64587, WO99/31236, EP1037977, WO00/17369, WO01/23533, WO0047618, WO00/58479, WO00/69262, WO01/00663, WO01/00665, U.S. Pat. No. 6,313,268.

BACE was found to be a pepsin-like aspartic proteinase, the mature enzyme consisting of the N-terminal catalytic domain, a transmembrane domain, and a small cytoplasmic domain. BACE has an optimum activity at pH 4.0-5.0 (Vassar et al, 1999) and is inhibited weakly by standard pepsin inhibitors such as pepstatin. It has been shown that the catalytic domain minus the transmembrane and cytoplasmic domain has activity against substrate peptides (Lin et al, 2000). BACE is a membrane bound type 1 protein that is synthesized as a partially active proenzyme, and is abundantly expressed in brain tissue. It is thought to represent the major β-secretase activity, and is considered to be the rate-limiting step in the production of amyloid-β-protein (Aβ). It is thus of special interest in the pathology of Alzheimer's disease, and in the development of drugs as a treatment for Alzheimer's disease.

Aβ or amyloid-β-protein is the major constituent of the brain plaques which are characteristic of Alzheimer's disease (De Strooper et al, 1999). Aβ is a 39-42 residue peptide formed by the specific cleavage of a class I transmembrane protein called APP, or amyloid precursor protein. Aβ-secretase activity cleaves this protein between residues Met671 and Asp672 (numbering of 770aa isoform of APP) to form the N-terminus of Aβ. A second cleavage of the peptide is associated with γ-secretase to form the C-terminus of the Aβ peptide.

Alzheimer's disease (AD) is estimated to afflict more than 20 million people worldwide and is believed to be the most common form of dementia. Alzheimer's disease is a progressive dementia in which massive deposits of aggregated protein breakdown products —amyloid plaques and neurofibrillary tangles accumulate in the brain. The amyloid plaques are thought to be responsible for the mental decline seen in Alzheimer's patients.

The likelihood of developing Alzheimer's disease increases with age, and as the aging population of the developed world increases, this disease becomes a greater and greater problem. In addition to this, there is a familial link to Alzheimer's disease and consequently any individuals possessing the double mutation of APP known as the Swedish mutation (in which the mutated APP forms a considerably improved substrate for BACE) have a much greater chance of developing AD, and also of developing it at an early age (see also U.S. Pat. No. 6,245,964 and U.S. Pat. No. 5,877,399 pertaining to transgenic rodents comprising APP-Swedish). Consequently, there is also a strong need for developing a compound that can be used in a prophylactic fashion for these individuals.

The gene encoding APP is found on chromosome 21, which is also the chromosome found as an extra copy in Down's syndrome. Down's syndrome patients tend to acquire Alzheimer's disease at an early age, with almost all those over 40 years of age showing Alzheimer's-type pathology (Oyama et al., 1994). This is thought to be due to the extra copy of the APP gene found in these patients, which leads to overexpression of APP and therefore to increased levels of APPβ causing the high prevalence of Alzheimer's disease seen in this population. Thus, inhibitors of BACE could be useful in reducing Alzheimer's-type pathology in Down's syndrome patients.

Drugs that reduce or block BACE activity should therefore reduce Aβ levels and levels of fragments of Aβ in the brain, or elsewhere where Aβ or fragments thereof deposit, and thus slow the formation of amyloid plaques and the progression of AD or other maladies involving deposition of Aβ or fragments thereof (Yankner, 1996; De Strooper and Konig, 1999). BACE is therefore an important candidate for the development of drugs as a treatment and/or prophylaxis of Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration.

It would therefore be useful to inhibit the deposition of Aβ and portions thereof by inhibiting BACE through inhibitors such as the compounds provided herein.

The therapeutic potential of inhibiting the deposition of Aβ has motivated many groups to isolate and characterize secretase enzymes and to identify their potential inhibitors (see, e.g., WO01/23533 A2, EP0855444, WO00/17369, WO00/58479, WO00/47618, WO00/77030, WO01/00665, WO01/00663, WO01/29563, WO02/25276, U.S. Pat. No. 5,942,400, U.S. Pat. No. 6,245,884, U.S. Pat. No. 6,221,667, U.S. Pat. No. 6,211,235, WO02/02505, WO02/02506, WO02/02512, WO02/02518, WO02/02520, WO02/14264, WO05/058311, WO05/097767, WO06/041404, WO06/041405, WO06/0065204, WO06/0065277, US2006287294, WO06/138265, US20050282826, US20050282825, US20060281729, WO06/138217, WO06/138230, WO06/138264, WO06/138265, WO06/138266, WO06/099379, WO06/076284, US20070004786, US20070004730, WO07/011833, WO07/011810, US20070099875, US20070099898, WO07/049532).

The compounds of the present invention show beneficial properties compared to the potential inhibitors known in the art, e.g. improved potency.

DISCLOSURE OF THE INVENTION

Provided herein are novel compounds that are active BACE inhibitors. Thus, in one aspect of the invention, there is provided compounds of structural formula I:

I wherein $R^1$ is selected from aryl and heteroaryl, wherein said aryl or heteroaryl is optionally substituted with one or more $R^4$; and wherein said aryl or heteroaryl is optionally fused with a 4, 5, 6 or 7 membered cycloalkyl, cycloalkenyl or heterocyclyl group to form a bicyclic ring system, wherein said bicyclic ring system is optionally substituted with one or more $R^4$;

$R^2$ is selected from aryl and heteroaryl, wherein said aryl or heteroaryl is optionally substituted with one or more $R^4$; and wherein said aryl or heteroaryl is optionally fused with a 4, 5, 6 or 7 membered cycloalkyl, cycloalkenyl or heterocyclyl group to form a bicyclic ring system, wherein said bicyclic ring system is optionally substituted with one or more $R^4$;

$R^3$ is independently selected from halogen, nitro, CHO, $CO_{0-6}$alkylCN, $OC_{1-6}$alkylCN, $C_{0-6}$alkylOR$^5$, $OC_{2-6}$alkylOR$^5$, $C_{0-6}$alkylNR$^5$R$^6$, $OC_{2-6}$alkylNR$^5$R$^6$, $OC_{2-6}$alkylOC$_{2-6}$alkylNR$^5$R$^6$, $C_{0-6}$alkylCO$_2$R$^5$, $OC_{1-6}$alkylCO$_2$R$^5$, $C_{0-6}$alkylCONR$^5$R$^6$, $OC_{1-6}$alkylCONR$^5$R$^6$, $OC_{2-6}$alkylNR$^5$(CO)R$^6$, $C_{0-6}$alkylNR$^5$(CO)R$^6$, O(CO)NR$^5$R$^6$, NR$^5$(CO)OR$^6$, NR$^5$(CO)NR$^5$R$^6$, O(CO)OR$^5$, O(CO)R$^5$, $C_{0-6}$alkylCOR$^5$, $OC_{1-6}$alkylCOR$^5$, NR$^5$(CO)(CO)R$^5$, NR$^5$(CO)(CO)NR$^5$R$^6$, $C_{0-6}$alkylSR$^5$, $C_{0-6}$alkyl(SO$_2$)NR$^5$R$^6$, $OC_{1-6}$alkylNR$^5$(SO$_2$)R$^6$, $OC_{0-6}$alkyl(SO$_2$)NR$^5$R$^6$, $C_{0-6}$alkyl(SO)NR$^5$R$^6$, $OC_{1-6}$alkyl(SO)NR$^5$R$^6$, $C_{0-6}$alkylOSO$_2$R$^5$, $C_{0-6}$alkylSO$_3$R$^5$, $C_{0-6}$alkylNR$^5$(SO$_2$)NR$^5$R$^6$, $C_{0-6}$alkylNR$^5$(SO)R$^6$, $OC_{2-6}$alkylNR$^5$(SO)R$^6$, $OC_{1-6}$alkylSO$_2$R$^5$, $C_{0-6}$alkylSO$_2$R$^5$, $C_{0-6}$alkylSOR$^5$, $C_{1-6}$alkyl, $C_{2-6}$alkenyl, $C_{2-6}$alkynyl, $C_{0-6}$alkylC$_{3-6}$cycloalkyl, $C_{0-6}$alkylC$_{3-6}$cycloalkenyl, $C_{0-6}$alkylC$_6$cycloalkynyl, $C_{0-6}$alkylaryl, $C_{0-6}$alkylheteroaryl, $C_{0-6}$alkylheterocyclyl and $OC_{2-6}$alkylheterocyclyl, wherein said $C_{1-6}$alkyl, $C_{2-6}$alkenyl, $C_{2-6}$alkynyl, $C_{0-6}$alkylC$_{3-6}$cycloalkyl, $C_{0-6}$alkylC$_{3-6}$cycloalkenyl, $C_{0-6}$alkylC$_6$cycloalkynyl, $C_{0-6}$alkylaryl, $C_{0-6}$alkylheteroaryl, $C_{0-6}$alkylheterocyclyl or $OC_{2-6}$alkylheterocyclyl is optionally substituted with one or more $R^{11}$, and wherein any of the individual aryl or heteroaryl groups may be optionally fused with a 4, 5, 6 or 7 membered cycloalkyl, cycloalkenyl or heterocyclyl group to form a bicyclic ring system where the bicyclic ring system is optionally substituted with one or more A;

W is C or N;
X is C or N;
Y is C or N;
Z is C or N;
provided that when:
W and X are N, Y and Z are C;
W and Y are N, X and Z are C;
W and Z are N, X and Y are C;
X and Y are N, W and Z are C;
X and Z are N, W and Y are C;
Y and Z are N, W and X are C;
W, X and Y are C, Z is N;
W, X and Z are C, Y is N;
W, Y and Z are C, X is N;
X, Y and Z are C, W=N;
m is 0, 1, 2 or 3;

$R^4$ is independently selected from halogen, nitro, SF$_5$, OSF$_5$, CHO, $C_{0-6}$alkylCN, $OC_{1-6}$alkylCN, $C_{0-6}$alkylOR$^5$, $OC_{2-6}$alkylOR$^5$, $C_{0-6}$alkylNR$^5$R$^6$, $OC_{2-6}$alkylNR$^5$R$^6$, $OC_{2-6}$alkylOC$_{2-6}$alkylNR$^5$R$^6$, $C_{0-6}$alkylCO$_2$R$^5$, $OC_{1-6}$alkylCO$_2$R$^5$ $C_{0-6}$alkylCONR$^5$R$^6$ $OC_{1-6}$alkylCONR$^5$R$^6$, $OC_{2-6}$alkylNR$^5$(CO)R$^6$, $C_{0-6}$alkylNR$^5$(CO)R$^6$, O(CO)NR$^5$R$^6$, NR$^5$(CO) OR$^6$, NR$^5$(CO)NR$^5$R$^6$, O(CO)OR$^5$, O(CO)R$^5$, $C_{0-6}$alkylCOR$^5$, $OC_{1-6}$alkylCOR$^5$, NR$^5$(CO)(CO)R$^5$, NR$^5$(CO)(CO) NR$^5$R$^6$, $C_{0-6}$alkylSR$^5$, $C_{0-6}$alkyl(SO$_2$)NR$^5$R$^6$, $OC_{1-6}$alkylNR$^5$(SO$_2$)R$^6$, $OC_{0-6}$alkyl(SO$_2$)NR$^5$R$^6$, $C_{0-6}$alkyl(SO) NR$^5$R$^6$, $OC_{1-6}$alkyl(SO)NR$^5$R$^6$, $C_{0-6}$alkylOSO$_2$R$^5$, SO$_3$R$^5$, $C_{0-6}$alkylNR$^5$(SO$_2$)NR$^5$R$^6$, $C_{0-6}$alkylNR$^5$(SO)R$^6$, $OC_{2-6}$alkylNR$^5$(SO)R$^6$, $OC_{1-6}$ alkylSO$_2$R$^5$, $C_{0-6}$alkylSO$_2$R$^5$, $C_{0-6}$alkylSOR$^5$, $C_{1-6}$alkyl, $C_{2-6}$alkenyl, $C_{2-6}$alkynyl, $C_{0-6}$alkylC$_{3-6}$cycloalkyl, $C_{0-6}$alkylC$_{3-6}$cycloalkenyl, $C_{0-6}$alkylC$_6$cycloalkynyl, $C_{0-6}$alkylaryl, $C_{0-6}$alkylheteroaryl, $C_{0-6}$alkylheterocyclyl and $OC_{2-6}$alkylheterocyclyl, wherein said $C_{1-6}$alkyl, $C_{2-6}$alkenyl, $C_{2-6}$alkynyl, $C_{0-6}$alkylC$_{3-6}$cycloalkyl, $C_{0-6}$alkylaryl, $C_{0-6}$alkylheteroaryl, $C_{0-6}$alkylheterocyclyl or $OC_{2-6}$alkylheterocyclyl is optionally substituted with one or more $R^{11}$, and wherein any of the individual aryl or heteroaryl groups may be optionally fused with a 4, 5, 6 or 7 membered cycloalkyl, cycloalkenyl or heterocyclyl group to form a bicyclic ring system where the bicyclic ring system is optionally substituted with one or more A;

$R^5$ is selected from hydrogen, $C_{1-6}$alkyl, $C_{2-6}$alkenyl, $C_{2-6}$alkynyl, $C_{0-6}$alkylC$_{3-6}$cycloalkyl, $C_{0-6}$alkylC$_{3-6}$cycloalkenyl, $C_{0-6}$alkylC$_6$cycloalkynyl, $C_{0-6}$alkylaryl, $C_{0-6}$alkylheteroaryl, $C_{0-6}$alkylheterocyclyl and $C_{1-6}$alkylNR$^7$R$^8$, wherein said $C_{1-6}$alkyl, $C_{2-6}$alkenyl, $C_{2-6}$alkynyl, $C_{0-6}$alkylC$_{3-6}$cycloalkyl, $C_{0-6}$alkylC$_{3-6}$cycloalkenyl, $C_{0-6}$alkylC$_6$cycloalkynyl, $C_{0-6}$alkylaryl, $C_{0-6}$alkylheteroaryl or $C_{0-6}$alkylheterocyclyl is optionally substituted with one or more A;

$R^6$ is selected from hydrogen and $C_{1-6}$alkyl, $C_{2-6}$alkenyl, $C_{2-6}$alkynyl, $C_{0-6}$alkylOR$^7$, $C_{0-6}$alkylC$_{3-6}$cycloalkyl, $C_{0-6}$alkylC$_{3-6}$cycloalkenyl, $C_{0-6}$alkylC$_6$cycloalkynyl, $C_{0-6}$alkylaryl, $C_{0-6}$alkylheteroaryl, $C_{0-6}$alkylheterocyclyl and $C_{1-6}$alkylNR$^7$R$^8$, wherein said $C_{1-6}$alkyl, $C_{2-6}$alkenyl, $C_{2-6}$alkynyl, $C_{0-6}$alkyl$C_{3-6}$cycloalkyl, $C_{0-6}$alkyl$C_{3-6}$cycloalkenyl, $C_{0-6}$alkyl$C_{6}$cycloalkynyl, $C_{0-6}$alkylaryl, $C_{0-6}$alkylheteroaryl or $C_{0-6}$alkylheterocyclyl is optionally substituted with one or more A; or $R^5$ and $R^6$ may together form a 4 to 6 membered heterocyclic ring containing one or more heteroatoms selected from N, O or S that is optionally substituted with A; whenever two $R^5$ groups occur in the structure then they may optionally together form a 5 or 6 membered heterocyclic ring containing one or more heteroatoms selected from N, O or S, that is optionally substituted with one or more A;

$R^7$ and $R^8$ are independently selected from hydrogen, $C_{1-6}$alkyl, $C_{2-6}$alkenyl, $C_{2-6}$alkynyl, $C_{0-6}$alkyl$C_{3-6}$cycloalkyl, $C_{O-6}$alkyl$C_{3-6}$cycloalkenyl, $C_{0-6}$alkyl$C_{6}$cycloalkynyl, $C_{0-6}$alkylaryl, $C_{0-6}$alkylheterocyclyl and $C_{0-6}$alkylheteroaryl, wherein said $C_{1-6}$alkyl, $C_{2-6}$alkenyl, $C_{2-6}$alkynyl, $C_{0-6}$alkyl$C_{3-6}$cycloalkyl, $C_{0-6}$alkyl$C_{3-6}$cycloalkenyl, $C_{0-6}$alkylC6cycloalkynyl, $C_{0-6}$alkylaryl, $C_{0-6}$alkylheteroaryl or $C_{0-6}$alkylheterocyclyl is optionally substituted with one or more A; or $R^7$ and $R^8$ may together form a 4 to 6 membered heterocyclic ring containing one or more heteroatoms selected from N, O or S optionally substituted with one or more A;

A is selected from oxo, halogen, nitro, $SF_5$, $OSF_5$, CN, $OR^9$, $C_{1-6}$alkyl, $C_{2-6}$alkenyl, $C_{2-6}$alkynyl, $C_{0-6}$alkylaryl, $C_{0-6}$alkylheteroaryl, $C_{0-6}$alkyl$C_{3-6}$cycloalkyl, $C_{0-6}$alkylheterocyclyl, fluoromethyl, difluoromethyl, trifluoromethyl, fluoromethoxy, difluoromethoxy, trifluoromethoxy, $OC_{2-6}$alkyl$NR^9R^{10}$, $NR^9R^{10}$, $CONR^9R^{10}$, $NR^9(CO)R^{10}$, $O(CO)C_{1-6}$alkyl, $(CO)OC_{1-6}$alkyl, $COR^9$, $(SO_2)NR^9R^{10}$, $NSO_2R^9$, $SO_2R^9$, $SOR^9$, $(CO)C_{1-6}$alkyl$NR^9R^{10}$, $(SO_2)C_{1-6}$alkyl$NR^9R^{10}$, $OSO_2R^9$ and $SO_3R^9$, wherein said $C_{1-6}$alkyl, $C_{2-6}$alkenyl, $C_{2-6}$alkynyl, $C_{0-6}$alkylaryl, $C_{0-6}$alkylheteroaryl, $C_{0-6}$alkylheterocyclyl, $C_{0-6}$alkyl$C_{3-6}$cycloalkyl, $C_{0-6}$alkyl$C_{3-6}$ cycloalkenyl or $C_{0-6}$alkyl$C_{6}$cycloalkynyl is optionally substituted with halo, $OSO_2R^9$, $SO_3R^9$, nitro, cyano, $OR^9$, $C_{1-6}$alkyl, fluoromethyl, difluoromethyl, trifluoromethyl, fluoromethoxy, difluoromethoxy or trifluoromethoxy; $R^9$ and $R^{10}$ are independently selected from hydrogen, $C_{1-6}$alkyl, $C_{2-6}$alkenyl, $C_{2-6}$alkynyl, $C_{3-6}$cycloalkyl, $C_{3-6}$cycloalkenyl, $C_{6}$cycloalkynyl, aryl, heteroaryl and heterocyclyl, wherein said $C_{1-6}$alkyl, $C_{2-6}$alkenyl, $C_{2-6}$alkynyl, $C_{3-6}$cycloalkyl, $C_{3-6}$cycloalkenyl, $C_{6}$cycloalkynyl, aryl, heteroaryl or heterocyclyl is optionally substituted with one, two or three hydroxy, cyano, halogen or $C_{1-3}$alkyloxy; or $R^9$ and $R^{10}$ may together form a 4 to 6 membered heterocyclic ring containing one or more heteroatoms selected from N, O or S optionally substituted with hydroxy, $C_{1-3}$alkyloxy, cyano or halogen;

$R^{11}$ is independently selected from halogen, nitro, $SF_5$, $OSF_5$, CHO, $C_{0-6}$alkylCN, $OC_{1-6}$alkylCN, $C_{0-6}$alkyl$OR^8$, $OC_{1-6}$alkyl$OR^8$, fluoromethoxy, difluoromethoxy, trifluoromethoxy, $C_{0-6}$alkyl$NR^5R^6$, $OC_{2-6}$alkyl$NR^5R^6$, $OC_{2-6}$alkyl$OC_{2-6}$alkyl$NR^5R^6$, $NR^5OR^6$, $C_{0-6}$alkyl$CO_2R^5$, $OC_{1-6}$alkyl$CO_2R^5$, $C_{0-6}$alkyl$CONR^5R^6$, $OC_{1-6}$alkyl$CONR^5R^6$, $OC_{2-6}$alkyl$NR^5(CO)R^6$, $C_{0-6}$alkyl$NR^5(CO)R^6$, $O(CO)NR^5R^6$, $NR^5(CO)OR^6$, $NR^5(CO)NR^5R^6$, $O(CO)OR^5$, $O(CO)R^5$, $C_{0-6}$alkyl$COR^5$, $OC_{1-6}$alkyl$COR^5$, $NR^5(CO)(CO)R^6$, $NR^5(CO)(CO)NR^5R^6$, $C_{0-6}$alkyl$SR^5$, $C_{0-6}$alkyl$(SO_2)NR^5R^6$, $OC_{2-6}$alkyl$NR^5(SO_2)R^6$, $OC_{0-6}$alkyl$(SO_2)NR^5R^6$, $C_{0-6}$alkyl$(SO)NR^5R^6$, $OC_{1-6}$alkyl$(SO)NR^5R^6$, $OSO_2R^5$, $SO_3R^5$, $C_{0-6}$alkyl$NR^5(SO_2)NR^5R^6$, $C_{0-6}$alkyl$NR^5(SO)R^6$, $OC_{2-6}$alkyl$NR^5(SO)R^6$, $OC_{1-6}$alkyl$SO_2R^5$, $C_{0-6}$alkyl$SO_2R^5$, $C_{0-6}$alkyl$SOR^5$, $C_{1-6}$alkyl, $C_{2-6}$alkenyl, $C_{2-6}$alkynyl, $C_{0-6}$alkyl$C_{3-6}$cycloalkyl, $C_{0-6}$alkyl$C_{3-6}$cycloalkenyl, $C_{0-6}$alkyl$C_{6}$cycloalkynyl, $C_{0-6}$alkylaryl, $C_{0-6}$alkylheteroaryl, $C_{0-6}$alkylheterocyclyl and $OC_{2-6}$alkylheterocyclyl, wherein said $C_{1-6}$alkyl, $C_{2-6}$alkenyl, $C_{2-6}$alkynyl, $C_{0-6}$alkyl$C_{3-6}$cycloalkyl, $C_{0-6}$alkyl$C_{3-6}$cycloalkenyl, $C_{0-6}$alkyl$C_{6}$cycloalkynyl, $C_{0-6}$alkylaryl, $C_{0-6}$alkylheteroaryl, $C_{0-6}$alkylheterocyclyl or $OC_{2-6}$alkylheterocyclyl is optionally substituted with one or more A;

as a free base or a pharmaceutically acceptable salt, solvate or solvate of a salt thereof.

In another aspect of the invention, there is provided compounds of formula I, wherein $R^1$ is selected from aryl and heteroaryl, wherein said aryl or heteroaryl is optionally substituted with one or more $R^4$;

$R^2$ is selected from aryl and heteroaryl, wherein said aryl or heteroaryl is optionally substituted with one or more $R^4$;

$R^3$ is independently selected from halogen, nitro, CHO, $C_{0-6}$alkylCN, $OC_{1-6}$alkylCN, $C_{0-6}$alkyl$OR^5$, $OC_{2-6}$alkyl$OR^5$, $CO_{0-6}$alkyl$NR^5R^6$, $OC_{2-6}$alkyl$NR^5R^6$, $OC_{2-6}$alkyl$OC_{2-6}$alkyl$NR^5R^6$, $C_{0-6}$alkyl$CO_2R^5$, $OC_{1-6}$alkyl$CO_2R^5$, $C_{0-6}$alkyl$CONR^5R^6$, $OC_{1-6}$alkyl$CONR^5R^6$, $OC_{2-6}$alkyl$NR^5(CO)R^6$, $C_{0-6}$alkyl$NR^5(CO)R^6$, $O(CO)NR^5R^6$, $NR^5(CO)OR^6$, $NR^5(CO)NR^5R^6$, $O(CO)OR^5$, $O(CO)R^5$, $C_{0-6}$alkyl$COR^5$, $OC_{1-6}$alkyl$COR^5$, $NR^5(CO)(CO)R^5$, $NR^5(CO)(CO)NR^5R^6$, $C_{0-6}$alkyl$SR^5$, $C_{0-6}$alkyl$(SO_2)NR^5R^6$, $OC_{1-6}$alkyl$NR^5(SO_2)R^6$, $OC_{0-6}$alkyl$(SO_2)NR^5R^6$, $C_{0-6}$alkyl$(SO)NR^5R^6$, $OC_{1-6}$alkyl$(SO)NR^5R^6$, $OSO_2R^5$, $SO_3R^5$, $C_{0-6}$alkyl$NR^5(SO_2)NR^5R^6$, $C_{0-6}$alkyl$NR^5(SO)R^6$, $OC_{2-6}$alkyl$NR^5(SO)R^6$, $OC_{1-6}$alkyl$SO_2R^5$, $C_{0-6}$alkyl$SO_2R^5$, $C_{0-6}$alkyl$SOR^5$, $C_{1-6}$alkyl, $C_{2-6}$alkenyl, $C_{2-6}$alkynyl, $C_{0-6}$alkyl$C_{3-6}$cycloalkyl, $C_{0-6}$alkyl$C_{3-6}$cycloalkenyl, $C_{0-6}$alkyl$C_{6}$cycloalkynyl, $C_{0-6}$alkylaryl, $C_{0-6}$alkylheteroaryl, $C_{0-6}$alkylheterocyclyl and $OC_{2-6}$alkylheterocyclyl, wherein said $C_{1-6}$alkyl, $C_{2-6}$alkenyl, $C_{2-6}$alkynyl, $C_{0-6}$alkyl$C_{3-6}$cycloalkyl, $C_{0-6}$alkyl$C_{3-6}$cycloalkenyl, $C_{0-6}$alkyl$C_{6}$cycloalkynyl, $C_{0-6}$alkylaryl, $C_{0-6}$alkylheteroaryl, $C_{0-6}$alkylheterocyclyl or $OC_{2-6}$alkylheterocyclyl is optionally substituted with one or more $R^{11}$, and wherein any of the individual aryl or heteroaryl groups may be optionally fused with a 4, 5, 6 or 7 membered cycloalkyl, cycloalkenyl or heterocyclyl group to form a bicyclic ring system where the bicyclic ring system is optionally substituted with one or more A;

W is C or N;
X is C or N;
Y is C or N;
Z is C or N;
provided that when:
W and X are N, Y and Z are C;
W and Y are N, X and Z are C;
W and Z are N, X and Y are C;
X and Y are N, W and Z are C;
X and Z are N, W and Y are C;
Y and Z are N, W and X are C;
W, X and Y are C, Z is N;
W, X and Z are C, Y is N;
W, Y and Z are C, X is N;
X, Y and Z are C, W=N;
m is 0, 1, 2 or 3;

$R^4$ is independently selected from halogen, nitro, $SF_5$, $OSF_5$, CHO, $C_{0-6}$alkylCN, $OC_{1-6}$alkylCN, $C_{0-6}$alkyl$OR^5$, $OC_{2-6}$alkyl$OR^5$, $C_{0-6}$alkyl$NR^5R^6$, $OC_{2-6}$alkyl$NR^5R^6$, $OC_{2-6}$alkyl$OC_{2-6}$alkyl$NR^5R^6$, $C_{0-6}$alkyl$CO_2R^5$, $OC_{1-6}$alkyl$CO_2R^5$, $C_{0-6}$alkyl$CONR^5R^6$ $OC_{1-6}$alkyl$CONR^5R^6$, $OC_{2-6}$alkyl$NR^5(CO)R^6$, $C_{0-6}$alkyl$NR^5(CO)R^6$, $O(CO)NR^5R^6$, $NR^5(CO)OR^6$, $NR^5(CO)NR^5R^6$, $O(CO)OR^5$, $O(CO)R^5$, $C_{0-6}$alkyl$COR^5$, $OC_{1-6}$alkyl$COR^5$, $NR^5(CO)(CO)R^5$, $NR^5(CO)(CO)NR^5R^6$, $C_{0-6}$alkyl$SR^5$, $C_{0-6}$alkyl$(SO_2)NR^5R^6$, $OC_{1-6}$alkyl$NR^5(SO_2)R^6$, $OC_{0-6}$alkyl$(SO_2)NR^5R^6$, $C_{0-6}$alkyl$(SO)$ $NR^5R^6$, $OC_{1-6}alkyl(SO)NR^5R^6$, $C_{0-6}alkylOSO_2R^5$, $SO_3R^5$, $C_{0-6}alkylNR^5(SO_2)NR^5R^6$, $C_{0-6}alkylNR^5(SO)R^6$, $OC_{2-6}alkylNR^5(SO)R^6$, $OC_{1-6}alkylSO_2R^5$, $C_{0-6}alkylSO_2R^5$, $C_{0-6}alkylSOR^5$, $C_{1-6}alkyl$, $C_{2-6}alkenyl$, $C_{2-6}alkynyl$, $C_{0-6}alkylC_{3-6}cycloalkyl$, $C_{0-6}alkylC_{3-6}cycloalkenyl$, $C_{0-6}alkylC_6cycloalkynyl$, $C_{0-6}alkylaryl$, $C_{0-6}alkylheteroaryl$, $C_{0-6}alkylheterocyclyl$ and $OC_{2-6}alkylheterocyclyl$, wherein said $C_{1-6}alkyl$, $C_{2-6}alkenyl$, $C_{2-6}alkynyl$, $C_{0-6}alkylC_{3-6}cycloalkyl$, $CO_{1-6}alkylaryl$, $C_{0-6}alkylheteroaryl$, $C_{0-6}alkylheterocyclyl$ or $OC_{2-6}alkylheterocyclyl$ is optionally substituted with one or more $R^{11}$, and wherein any of the individual aryl or heteroaryl groups may be optionally fused with a 4, 5, 6 or 7 membered cycloalkyl, cycloalkenyl or heterocyclyl group to form a bicyclic ring system where the bicyclic ring system is optionally substituted with one or more A;

$R^5$ is selected from hydrogen, $C_{1-6}alkyl$, $C_{2-6}alkenyl$, $C_{2-6}alkynyl$, $C_{0-6}alkylC_{3-6}cycloalkyl$, $C_{0-6}alkylC_{3-6}cycloalkenyl$, $C_{0-6}alkylC_6cycloalkynyl$, $C_{0-6}alkylaryl$, $C_{0-6}alkylheteroaryl$, $C_{0-6}alkylheterocyclyl$ and $C_{1-6}alkylNR^7R^8$, wherein said $C_{1-6}alkyl$, $C_{2-6}alkenyl$, $C_{2-6}alkynyl$, $C_{0-6}alkylC_{3-6}cycloalkyl$, $C_{0-6}alkylC_{3-6}cycloalkenyl$, $C_{0-6}alkylC_6cycloalkynyl$, $C_{0-6}alkylaryl$, $C_{0-6}alkylheteroaryl$ or $C_{0-6}alkylheterocyclyl$ is optionally substituted with one or more A;

$R^6$ is selected from hydrogen and $C_{1-6}alkyl$, $C_{2-6}alkenyl$, $C_{2-6}alkynyl$, $C_{0-6}alkylOR^7$, $C_{0-6}alkylC_{3-6}cycloalkyl$, $C_{0-6}alkylC_{3-6}cycloalkenyl$, $C_{0-6}alkylC_6cycloalkynyl$, $C_{0-6}alkylaryl$, $C_{0-6}alkylheteroaryl$, $C_{0-6}alkylheterocyclyl$ and $C_{1-6}alkylNR^7R^8$, wherein said $C_{1-6}alkyl$, $C_{2-6}alkenyl$, $C_{2-6}alkynyl$, $C_{0-6}alkylC_{3-6}cycloalkyl$, $C_{0-6}alkylC_{3-6}cycloalkenyl$, $C_{0-6}alkylC_6cycloalkynyl$, $C_{0-6}alkylaryl$, $C_{0-6}alkylheteroaryl$ or $C_{0-6}alkylheterocyclyl$ is optionally substituted with one or more A; or $R^5$ and $R^6$ may together form a 4 to 6 membered heterocyclic ring containing one or more heteroatoms selected from N, O or S that is optionally substituted with A; whenever two $R^5$ groups occur in the structure then they may optionally together form a 5 or 6 membered heterocyclic ring containing one or more heteroatoms selected from N, O or S, that is optionally substituted with one or more A;

$R^7$ and $R^8$ are independently selected from hydrogen, $C_{1-6}alkyl$, $C_{2-6}alkenyl$, $C_{2-6}alkynyl$, $C_{0-6}alkylC_{3-6}cycloalkyl$, $C_{0-6}alkylC_{3-6}cycloalkenyl$, $C_{0-6}alkylC_6cycloalkynyl$, $C_{0-6}alkylaryl$, $C_{0-6}alkylheterocyclyl$ and $C_{0-6}alkylheteroaryl$, wherein said $C_{1-6}alkyl$, $C_{2-6}alkenyl$, $C_{2-6}alkynyl$, $C_{0-6}alkylC_{3-6}cycloalkyl$, $C_{0-6}alkylC_{3-6}cycloalkenyl$, $C_{0-6}alkylC_6cycloalkynyl$, $C_{0-6}alkylaryl$, $C_{0-6}alkylheteroaryl$ or $C_{0-6}alkylheterocyclyl$ is optionally substituted with one or more A; or $R^7$ and $R^8$ may together form a 4 to 6 membered heterocyclic ring containing one or more heteroatoms selected from N, O or S optionally substituted with one or more A;

A is selected from oxo, halogen, nitro, $SF_5$, $OSF_5$, CN, $OR^9$, $C_{1-6}alkyl$, $C_{2-6}alkenyl$, $C_{2-6}alkynyl$, $C_{0-6}alkylaryl$, $C_{0-6}alkylheterocyclyl$, $C_{0-6}alkylC_{3-6}cycloalkyl$, $C_{0-6}alkylheterocyclyl$, fluoromethyl, difluoromethyl, trifluoromethyl, fluoromethoxy, difluoromethoxy, trifluoromethoxy, $OC_{2-6}alkylNR^9R^{10}$, $NR^9R^{10}$, $CONR^9R^{10}$, $NR^9(CO)R^{10}$, $O(CO)C_{1-6}alkyl$, $(CO)OC_{1-6}alkyl$, $COR^9$, $(SO_2)NR^9R^{10}$, $NSO_2R^9$, $SO_2R^9$, $SOR^9$, $(CO)C_{1-6}alkylNR^9R^{10}$, $(SO_2)C_{1-6}alkylNR^9R^{10}$, $OSO_2R^9$ and $SO_3R^9$, wherein said $C_{1-6}alkyl$, $C_{2-6}alkenyl$, $C_{2-6}alkynyl$, $C_{0-6}alkylaryl$, $C_{0-6}alkylheteroaryl$, $C_{0-6}alkylheterocyclyl$, $C_{0-6}alkylC_{3-6}cycloalkyl$, $C_{0-6}alkylC_{3-6}cycloalkenyl$ or $C_{0-6}alkylC_6cycloalkynyl$ is optionally substituted with halo, $OSO_2R^9$, $SO_3R^9$, nitro, cyano, $OR^9$, $C_{1-6}alkyl$, fluoromethyl, difluoromethyl, trifluoromethyl, fluoromethoxy, difluoromethoxy or trifluoromethoxy;

$R^9$ and $R^{10}$ are independently selected from hydrogen, $C_{1-6}alkyl$, $C_{2-6}alkenyl$, $C_{2-6}alkynyl$, $C_{3-6}cycloalkyl$, $C_{3-6}cycloalkenyl$, $C_6cycloalkynyl$, aryl, heteroaryl and heterocyclyl, wherein said $C_{1-6}alkyl$, $C_{2-6}alkenyl$, $C_{2-6}alkynyl$, $C_{3-6}cycloalkyl$, $C_{3-6}cycloalkenyl$, $C_6cycloalkynyl$, aryl, heteroaryl or heterocyclyl is optionally substituted with one, two or three hydroxy, cyano, halogen or $C_{1-3}alkyloxy$; or $R^9$ and $R^{10}$ may together form a 4 to 6 membered heterocyclic ring containing one or more heteroatoms selected from N, O or S optionally substituted with hydroxy, $C_{1-3}alkyloxy$, cyano or halogen;

$R^{11}$ is independently selected from halogen, nitro, $SF_5$, $OSF_5$, CHO, $C_{0-6}alkylCN$, $OC_{1-6}alkylCN$, $C_{0-6}alkylOR^8$, $OC_{1-6}alkylOR^8$, fluoromethoxy, difluoromethoxy, trifluoromethoxy, $C_{0-6}alkylNR^5R^6$, $OC_{2-6}alkylNR^5R^6$, $OC_{2-6}alkyl$ $OC_{2-6}alkylNR^5R^6$, $NR^5OR^6$, $C_{0-6}alkylCO_2R^5$, $OC_{1-6}alkylCO_2R^5$, $C_{0-6}alkylCONR^5R^6$, $OC_{1-6}alkylCONR^5R^6$, $OC_{2-6}alkylNR^5(CO)R^6$, $C_{0-6}alkylNR^5(CO)R^6$, $O(CO)NR^5R^6$, $NR^5(CO)OR^6$, $NR^5(CO)NR^5R^6$, $O(CO)OR^5$, $O(CO)R^5$, $C_{0-6}alkylCOR^5$, $OC_{1-6}alkylCOR^5$, $NR^5(CO)(CO)R^6$, $NR^5(CO)(CO)NR^5R^6$, $C_{0-6}alkylSR^5$, $C_{0-6}alkyl(SO_2)NR^5R^6$, $OC_{2-6}alkylNR^5(SO_2)R^6$, $OC_{0-6}alkyl(SO_2)NR^5R^6$, $C_{0-6}alkyl(SO)NR^5R^6$, $OC_{1-6}alkyl(SO)NR^5R^6$, $OSO_2R^5$, $SO_3R^5$, $C_{0-6}alkylNR^5(SO_2)NR^5R^6$, $C_{0-6}alkylNR^5(SO)R^6$, $OC_{2-6}alkylNR^5(SO)R^6$, $OC_{1-6}alkylSO_2R^5$, $C_{0-6}alkylSO_2R^5$, $C_{0-6}alkylSOR^5$, $C_{1-6}alkyl$, $C_{2-6}alkenyl$, $C_{2-6}alkynyl$, $C_{0-6}alkylC_{3-6}cycloalkyl$, $C_{0-6}alkylC_{3-6}cycloalkenyl$, $C_{0-6}alkylC_6cycloalkynyl$, $C_{0-6}alkylaryl$, $C_{0-6}alkylheteroaryl$, $C_{0-6}alkylheterocyclyl$ and $OC_{2-6}alkylheterocyclyl$, wherein said $C_{1-6}alkyl$, $C_{2-6}alkenyl$, $C_{2-6}alkynyl$, $C_{0-6}alkylC_{3-6}cycloalkyl$, $C_{0-6}alkylC_{3-6}cycloalkenyl$, $C_{0-6}alkylC_6cycloalkynyl$, $C_{0-6}alkylaryl$, $C_{0-6}alkylheteroaryl$, $C_{0-6}alkylheterocyclyl$ or $OC_{2-6}alkylheterocyclyl$ is optionally substituted with one or more A;

as a free base or a pharmaceutically acceptable salt, solvate or solvate of a salt thereof.

In another aspect of the invention, there is provided compounds of formula I, wherein X is C or N; Y is C; Z is C or N; and W is C.

In another aspect of the invention, there is provided compounds of formula I, wherein X is C; Y is C; Z is N; and W is C.

In another aspect of the invention, there is provided compounds of formula I, wherein m is 0.

In another aspect of the invention, there is provided compounds of formula I, wherein $R^1$ is aryl, wherein said aryl is optionally substituted with one $R^4$.

In another aspect of the invention, there is provided compounds of formula I, wherein $R^1$ is phenyl, substituted with one $R^4$.

In another aspect of the invention, there is provided compounds of formula I, wherein $R^4$ is $C_{0-6}alkylheteroaryl$, wherein said $C_{0-6}alkylheteroaryl$ is optionally substituted with one or more $R^{11}$.

In another aspect of the invention, there is provided compounds of formula I, wherein $R^4$ is pyrimidyl.

In another aspect of the invention, there is provided compounds of formula I, wherein $R^4$ is pyridyl.

In another aspect of the invention, there is provided compounds of formula I, wherein $R^4$ is pyridyl, substituted with one $R^{11}$, said $R^{11}$ being halo.

In another aspect of the invention, there is provided compounds of formula I, wherein $R^4$ is pyridyl, substituted with one $R^{11}$, said $R^{11}$ being $C_{0-6}$alkylOR$^5$; wherein said $C_{0-6}$alkylOR$^5$ represents methoxy.

In another aspect of the invention, there is provided compounds of formula I, wherein $R^4$ is $C_{0-6}$alkylaryl, wherein said $C_{0-6}$alkylaryl is optionally substituted with one or more $R^{11}$.

In another aspect of the invention, there is provided compounds of formula I, wherein $R^4$ represents phenyl substituted with two $R^{11}$, said $R^{11}$ being one halo and one $C_{0-6}$alkylOR$^5$; wherein said $C_{0-6}$alkylOR$^5$ represents methoxy.

In another aspect of the invention, there is provided compounds of formula I, wherein $R^2$ is heteroaryl in one embodiment of this aspect, said heteroaryl is pyridyl.

In another aspect of the invention, there is provided compounds of formula I, wherein $R^2$ is aryl substituted with one $R^{11}$. In one embodiment of this aspect, said $R^{11}$ represents $C_{0-6}$alkylOR$^5$; wherein said $C_{0-6}$alkylOR$^5$ represents methoxy.

In another aspect of the invention, there is provided compounds of formula I, wherein X is N; W is C; Y is C; and Z is C.

In one embodiment of this aspect, m is 0.

In another embodiment of this aspect, $R^1$ is $C_{0-6}$alkylaryl, optionally substituted with one $R^4$.

In another embodiment of this aspect, $R^1$ is phenyl, substituted with one $R^4$.

In another embodiment of this aspect, $R^4$ is $C_{0-6}$alkylheteroaryl, wherein said $C_{0-6}$alkylheteroaryl is optionally substituted with one or more $R^{11}$.

In another embodiment of this aspect, $R^4$ is pyrimidyl.

In another embodiment of this aspect, $R^4$ is pyridyl substituted with one $R^{11}$, said $R^{11}$ being halo.

In another embodiment of this aspect, $R^2$ is heteroaryl, said heteroaryl being pyridyl.

In another embodiment of this aspect,
$R^1$ is aryl, wherein said aryl is substituted with one $R^4$;
$R^2$ is selected from aryl and heteroaryl, wherein said aryl or heteroaryl is optionally substituted with one $R^4$;
W is C;
X is C or N;
Y is C;
Z is C or N;
m is 0;
$R^4$ is independently selected from $C_{0-6}$alkylOR$^5$, $C_{0-6}$alkylaryl and $C_{0-6}$alkylheteroaryl, wherein said $C_{0-6}$alkylaryl or $C_{0-6}$alkylheteroaryl is optionally substituted with one or more $R^{11}$;
$R^5$ is $C_{1-6}$alkyl;
$R^8$ is $C_{1-6}$alkyl;
$R^{11}$ is independently selected from halogen and $C_{0-6}$alkylOR$^8$.

In another aspect of the invention, there is provided compounds of formula I, wherein X is C; W is N; Y is C; and Z is C.

In one embodiment of this aspect, m is 0.

In another embodiment of this aspect, $R^1$ is $C_{0-6}$alkylaryl, optionally substituted with one $R^4$.

In another embodiment of this aspect, $R^1$ is phenyl, substituted with one $R^4$.

In another embodiment of this aspect, $R^4$ is $C_{0-6}$alkylheteroaryl or $C_{0-6}$alkylaryl, wherein said $C_{0-6}$alkylheteroaryl or $C_{0-6}$alkylaryl is optionally substituted with one or more $R^{11}$.

In another embodiment of this aspect, wherein $R^4$ is $C_{0-6}$alkylheteroaryl, wherein said $C_{0-6}$alkylheteroaryl is optionally substituted with one or more $R^{11}$.

In another embodiment of this aspect, $R^4$ is pyrimidyl.

In another embodiment of this aspect, $R^4$ is pyridyl substituted with one $R^{11}$, said $R^{11}$ being halo.

In another embodiment of this aspect, $R^4$ is phenyl substituted with two $R^{11}$, said $R^{11}$ being independently selected from halogen and $C_{0-6}$alkylOR$^8$.

In another embodiment of this aspect, $R^2$ is pyridyl.

In another embodiment of this aspect,
$R^1$ is aryl, wherein said aryl is substituted with one $R^4$;
$R^2$ is heteroaryl;
W is N;
X is C;
Y is C;
Z is C;
m is 0;
$R^4$ is independently selected from $C_{0-6}$alkylaryl and $C_{0-6}$alkylheteroaryl, wherein said $C_{0-6}$alkylaryl or $C_{0-6}$alkylheteroaryl is optionally substituted with one or more $R^{11}$;
$R^{11}$ is independently selected from halogen and $C_{0-6}$alkylOR$^8$.

In another aspect of the invention, there is provided compounds of formula I, selected from:
5-(4-Methoxyphenyl)-5-(3-pyrimidin-5-ylphenyl)-5H-pyrrolo[3,4-b]pyridin-7-amine;
5-[3-(2-Fluoropyridin-3-yl)phenyl]-5-(4-methoxyphenyl)-5H-pyrrolo[3,4-b]pyridin-7-amine;
5-(4-Methoxyphenyl)-5-[3-(5-methoxypyridin-3-yl)phenyl]-5H-pyrrolo[3,4-b]pyridin-7-amine;
5-(4-Methoxyphenyl)-5-(3-pyridin-3-ylphenyl)-5H-pyrrolo[3,4-b]pyridin-7-amine;
5-[3-(2-Fluoropyridin-3-yl)phenyl]-5-pyridin-4-yl-5H-pyrrolo[3,4-b]pyridin-7-amine;
5-Pyridin-4-yl-5-(3-pyrimidin-5-ylphenyl)-5H-pyrrolo[3,4-b]pyridin-7-amine;
5-(2'-Fluoro-5'-methoxybiphenyl-3-yl)-5-pyridin-4-yl-5H-pyrrolo[3,4-b]pyridin-7-amine 0.25 acetate;
5-(2'-Fluoro-3'-methoxybiphenyl-3-yl)-5-pyridin-4-yl-5H-pyrrolo[3,4-b]pyridin-7-amine 0.5 acetate;
3-Pyridin-4-yl-3-(3-pyrimidin-5-ylphenyl)-3H-pyrrolo[3,4-c]pyridin-1-amine; 3-[3-(2-Fluoropyridin-3-yl)phenyl]-3-pyridin-4-yl-3H-pyrrolo[3,4-c]pyridin-1-amine;
7-[3-(2-Fluoropyridin-3-yl)phenyl]-7-pyridin-4-yl-7H-pyrrolo[3,4-b]pyridin-5-amine;
7-Pyridin-4-yl-7-(3-pyrimidin-5-ylphenyl)-7H-pyrrolo[3,4-b]pyridin-5-amine; and
7-(2'-Fluoro-3'-methoxybiphenyl-3-yl)-7-pyridin-4-yl-7H-pyrrolo[3,4-b]pyridin-5-amine; as a free base or a pharmaceutically acceptable salt, solvate or solvate of a salt thereof.

In another aspect of the invention, there is provided a pharmaceutical formulation comprising as active ingredient a therapeutically effective amount of a compound according to formula I in association with pharmaceutically acceptable excipients, carriers or diluents.

In another aspect of the invention, there is provided a compound according to formula I for use as a medicament.

In another aspect of the invention, there is provided use of a compound according to formula I as a medicament for treating or preventing an Aβ-related pathology.

In another aspect of the invention, there is provided use of a compound according to formula I, as a medicament for treating or preventing an Aβ-related pathology, wherein said Aβ-related pathology is Downs syndrome, a β-amyloid angiopathy, cerebral amyloid angiopathy, hereditary cerebral hemorrhage, a disorder associated with cognitive impairment, MCI ("mild cognitive impairment"), Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

In another aspect of the invention, there is provided use of a compound according to formula I, in the manufacture of a medicament for treating or preventing an Aβ-related pathology.

In another aspect of the invention, there is provided use of a compound according to formula I, in the manufacture of a medicament for treating or preventing an Aβ-related pathology, wherein said Aβ-related pathology is Downs syndrome, a β-amyloid angiopathy, cerebral amyloid angiopathy, hereditary cerebral hemorrhage, a disorder associated with cognitive impairment, MCI ("mild cognitive impairment"), Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

In another aspect of the invention, there is provided a method of inhibiting activity of BACE comprising contacting said BACE with a compound according to formula I.

In another aspect of the invention, there is provided a method of treating or preventing an Aβ-related pathology in a mammal, comprising administering to said patient a therapeutically effective amount of a compound according to formula I.

In another aspect of the invention, there is provided a method of treating or preventing an Aβ-related pathology in a mammal, comprising administering to said patient a therapeutically effective amount of a compound according to formula I, wherein said Aβ-related pathology is Downs syndrome, a β-amyloid angiopathy, cerebral amyloid angiopathy, hereditary cerebral hemorrhage, a disorder associated with cognitive impairment, MCI ("mild cognitive impairment"), Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

In another aspect of the invention, there is provided a method of treating or preventing an Aβ-related pathology in a mammal, comprising administering to said patient a therapeutically effective amount of a compound according to formula I, wherein said mammal is a human.

In another aspect of the invention, there is provided a method of treating or preventing an Aβ-related pathology in a mammal, comprising administering to said patient a therapeutically effective amount of a compound according to formula I, and at least one cognitive enhancing agent, memory enhancing agent, or choline esterase inhibitor.

In another aspect of the invention, there is provided a method of treating or preventing an Aβ-related pathology in a mammal, comprising administering to said patient a therapeutically effective amount of a compound according to formula I, and at least one cognitive enhancing agent, memory enhancing agent, or choline esterase inhibitor wherein said Aβ-related pathology is Downs syndrome, a β-amyloid angiopathy, cerebral amyloid angiopathy, hereditary cerebral hemorrhage, a disorder associated with cognitive impairment, MCI ("mild cognitive impairment"), Alzheimer Dis-ease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

In another aspect of the invention, there is provided a method of treating or preventing an Aβ-related pathology in a mammal, comprising administering to said patient a therapeutically effective amount of a compound according to formula I, and at least one cognitive enhancing agent, memory enhancing agent, or choline esterase inhibitor, wherein said mammal is a human.

Some compounds of formula may have stereogenic centres and/or geometric isomeric centres (E- and Z- isomers), and it is to be understood that the invention encompasses all such optical isomers, enantiomers, diastereoisomers, atropisomers and geometric isomers.

The present invention relates to the use of compounds of formula I as hereinbefore defined as well as to the salts thereof. Salts for use in pharmaceutical compositions will be pharmaceutically acceptable salts, but other salts may be useful in the production of the compounds of formula I.

It is to be understood that the present invention relates to any and all tautomeric forms of the compounds of formula I.

Compounds of the invention can be used as medicaments. In some embodiments, the present invention provides compounds of formula I, or pharmaceutically acceptable salts, tautomers or in vivo-hydrolysable precursors thereof, for use as medicaments. In some embodiments, the present invention provides compounds described here in for use as as medicaments for treating or preventing an Aβ-related pathology. In some further embodiments, the Aβ-related pathology is Downs syndrome, a β-amyloid angiopathy, cerebral amyloid angiopathy, hereditary cerebral hemorrhage, a disorder associated with cognitive impairment, MCI ("mild cognitive impairment"), Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

In some embodiments, the present invention provides use of compounds of formula I or pharmaceutically acceptable salts, tautomers or in vivo-hydrolysable precursors thereof, in the manufacture of a medicament for the treatment or prophylaxis of Aβ-related pathologies. In some further embodiments, the Aβ-related pathologies include such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration.

In some embodiments, the present invention provides a method of inhibiting activity of BACE comprising contacting the BACE with a compound of the present invention. BACE is thought to represent the major β-secretase activity, and is considered to be the rate-limiting step in the production of amyloid-β-protein (Aβ). Thus, inhibiting BACE through inhibitors such as the compounds provided herein would be useful to inhibit the deposition of Aβ and portions thereof. Because the deposition of Aβ and portions thereof is linked to diseases such Alzheimer Disease, BACE is an important candidate for the development of drugs as a treatment and/or prophylaxis of Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration.

In some embodiments, the present invention provides a method for the treatment of Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration, comprising administering to a mammal (including human) a therapeutically effective amount of a compound of formula I, or a pharmaceutically acceptable salt, tautomer or in vivo-hydrolysable precursor thereof.

In some embodiments, the present invention provides a method for the prophylaxis of Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration comprising administering to a mammal (including human) a therapeutically effective amount of a compound of formula I or a pharmaceutically acceptable salt, tautomer or in vivo-hydrolysable precursors.

In some embodiments, the present invention provides a method of treating or preventing Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration by administering to a mammal (including human) a compound of formula I or a pharmaceutically acceptable salt, tautomer or in vivo-hydrolysable precursors and a cognitive and/or memory enhancing agent. Cognitive enhancing agents, memory enhancing agents and choline esterase inhibitors includes, but not limited to, onepezil (Aricept), galantamine (Reminyl or Razadyne), rivastigmine (Exelon), tacrine (Cognex) and memantine (Namenda, Axura or Ebixa).

In some embodiments, the present invention provides a method of treating or preventing Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration by administering to a mammal (including human) a compound of formula I or a pharmaceutically acceptable salt, tautomer or in vivo-hydrolysable precursors thereof wherein constituent members are provided herein, and a choline esterase inhibitor or anti-inflammatory agent.

In some embodiments, the present invention provides a method of treating or preventing Aβ-related pathologies such as Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer disease or dementia including dementia of mixed vascular and degenerative origin, pre-senile dementia, senile dementia and dementia associated with Parkinson's disease, progressive supranuclear palsy or cortical basal degeneration, or any other disease, disorder, or condition described herein, by administering to a mammal (including human) a compound of the present invention and an atypical antipsychotic agent. Atypical antipsychotic agents includes, but not limited to, Olanzapine (marketed as Zyprexa), Aripiprazole (marketed as Abilify), Risperidone (marketed as Risperdal), Quetiapine (marketed as Seroquel), Clozapine (marketed as Clozaril), Ziprasidone (marketed as Geodon) and Olanzapine/Fluoxetine (marketed as Symbyax).

In some embodiments, the mammal or human being treated with a compound of the invention has been diagnosed with a particular disease or disorder, such as those described herein. In these cases, the mammal or human being treated is in need of such treatment. Diagnosis, however, need not be previously performed.

The present invention also includes pharmaceutical compositions which contain, as the active ingredient, one or more of the compounds of the invention herein together with at least one pharmaceutically acceptable carrier, diluent or excipent.

The definitions set forth in this application are intended to clarify terms used throughout this application. The term "herein" means the entire application.

A variety of compounds in the present invention may exist in particular geometric or stereoisomeric forms. The present invention takes into account all such compounds, including cis- and trans isomers, R- and S- enantiomers, diastereomers, (D)-isomers, (L)-isomers, the racemic mixtures thereof, and other mixtures thereof, as being covered within the scope of this invention. Additional asymmetric carbon atoms may be present in a substituent such as an alkyl group. All such isomers, as well as mixtures thereof, are intended to be included in this invention. The compounds herein described may have asymmetric centers. Compounds of the present invention containing an asymmetrically substituted atom may be isolated in optically active or racemic forms. It is well known in the art how to prepare optically active forms, such as by resolution of racemic forms, by synthesis from optically active starting materials, or synthesis using optically active reagents. When required, separation of the racemic material can be achieved by methods known in the art. Many geometric isomers of olefins, C═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

It is noted that the carbon atoms for formula I may be replaced with 1 to 3 silicon atoms so long as all valency requirements are satisfied.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents, positions of substituents and/or variables are permissible only if such combinations result in stable compounds.

As used in this application, the term "optionally substituted," means that substitution is optional and therefore it is possible for the designated atom or moiety to be unsubstituted. In the event a substitution is desired then such substitution means that any number of hydrogens on the designated atom or moiety is replaced with a selection from the indicated group, provided that the normal valency of the designated atom or moiety is not exceeded, and that the substitution results in a stable compound. For example when a substituent is methyl (i.e., $CH_3$), then 3 hydrogens on the carbon atom can be replaced. Examples of such substituents include, but are not limited to: halogen, CN, $NH_2$, OH, SO, $SO_2$, COOH, $OC_{1-6}$alkyl, $CH_2OH$, $SO_2H$, $C_{1-6}$alkyl, $OC_{1-6}$alkyl, C(═O)$C_{1-6}$alkyl, C(═O)O$C_{1-6}$alkyl, C(═O)$NH_2$, C(═O)NH$C_{1-6}$alkyl, C(═O)N($C_{1-6}$alkyl)2, $SO_2C_{1-6}$alkyl, $SO_2$NH$C_{1-6}$alkyl, $SO_2$N($C_{1-6}$alkyl)2, NH($C_{1-6}$alkyl), N($C_{1-6}$alkyl)2, NHC(═O)$C_{1-6}$alkyl, NC(═O)($C_{1-6}$alkyl)$_2$, $C_{5-6}$aryl, $OC_{5-6}$aryl, C(═O)$C_{5-6}$aryl, C(═O)O$C_{5-6}$aryl, C(═O)NH$C_{5-6}$aryl, C(═O)N($C_{5-6}$aryl)2, $SO_2C_{5-6}$aryl, $SO_2$NH$C_{5-6}$aryl, $SO_2$N($C_{5-6}$aryl)$_2$, NH($C_{5-6}$aryl), N($C_{5-6}$aryl)$_2$, NC(═O)$C_{5-6}$aryl, NC(═O)($C_{5-6}$aryl)$_2$, $C_{5-6}$heterocyclyl, $OC_{5-6}$heterocyclyl, C(═O)$C_{5-6}$heterocyclyl, C(═O)O$C_{5-6}$heterocyclyl, C(═O)NH$C_{5-6}$heterocyclyl, C(═O)N($C_{5-6}$heterocyclyl)2, $SO_2C_{5-6}$heterocyclyl, $SO_2$NH$C_{5-6}$heterocyclyl, $SO_2$N($C_{5-6}$heterocyclyl)$_2$, NH($C_{5-6}$heterocyclyl), N($C_{5-6}$heterocyclyl)$_2$, NC(═O)$C_{5-6}$heterocyclyl, NC(═O)($C_{5-6}$heterocyclyl)$_2$.

As used herein, "alkyl", used alone or as a suffix or prefix, is intended to include both branched and straight chain saturated aliphatic hydrocarbon groups having from 1 to 12 carbon atoms or if a specified number of carbon atoms is provided then that specific number would be intended. For example "$C_{0-6}$ alkyl" denotes alkyl having 0, 1, 2, 3, 4, 5 or 6 carbon atoms. Examples of alkyl include, but are not limited to, methyl, ethyl, n-propyl, i-propyl, n-butyl, i-butyl, sec-butyl, t-butyl, pentyl, and hexyl. In the case where a subscript is the integer 0 (zero) the group to which the subscript refers to indicates that the group may be absent, i.e. there is a direct bond between the groups.

As used herein, "alkenyl" used alone or as a suffix or prefix is intended to include both branched and straight-chain alkene or olefin containing aliphatic hydrocarbon groups having from 2 to 12 carbon atoms or if a specified number of carbon atoms is provided then that specific number would be intended. For example "$C_{2-6}$alkenyl" denotes alkenyl having 2, 3, 4, 5 or 6 carbon atoms. Examples of alkenyl include, but are not limited to, vinyl, allyl, 1-propenyl, 1-butenyl, 2-butenyl, 3-butenyl, 2-methylbut-2-enyl, 3-methylbut-1-enyl, 1-pentenyl, 3-pentenyl and 4-hexenyl.

As used herein, "alkynyl" used alone or as a suffix or prefix is intended to include both branched and straight-chain alkyne containing aliphatic hydrocarbon groups having from 2 to 12 carbon atoms or if a specified number of carbon atoms is provided then that specific number would be intended. For example "$C_{2-6}$alkynyl" denotes alkynyl having 2, 3, 4, 5 or 6 carbon atoms. Examples of alkynyl include, but are not limited to, ethynyl, 1 -propynyl, 2-propynyl, 3-butynyl, -pentynyl, hexynyl and 1-methylpent-2-ynyl.

As used herein, "aromatic" refers to hydrocarbonyl groups having one or more unsaturated carbon ring(s) having aromatic characters, (e.g. 4n +2 delocalized electrons) and comprising up to about 14 carbon atoms. In addition "heteroaromatic" refers to groups having one or more unsaturated rings containing carbon and one or more heteroatoms such as nitrogen, oxygen or sulphur having aromatic character (e.g. 4n+2 delocalized electrons).

As used herein, the term "aryl" refers to an aromatic ring structure made up of from 5 to 14 carbon atoms. Ring structures containing 5, 6, 7 and 8 carbon atoms would be single-ring aromatic groups, for example, phenyl. Ring structures containing 8, 9, 10, 11, 12, 13, or 14 would be polycyclic, for example naphthyl. The aromatic ring can be substituted at one or more ring positions with such substituents as described above. The term "aryl" also includes polycyclic ring systems having two or more cyclic rings in which two or more carbons are common to two adjoining rings (the rings are "fused rings") wherein at least one of the rings is aromatic, for example, the other cyclic rings can be cycloalkyls, cycloalkenyls, cycloalkynyls, aryls and/or heterocyclyls. The terms ortho, meta and para apply to 1,2-, 1,3- and 1,4-disubstituted benzenes, respectively. For example, the names 1,2-dimethylbenzene and ortho-dimethylbenzene are synonymous.

As used herein, the term "cycloalkyl" is intended to include saturated ring groups, having the specified number of carbon atoms. These may include fused or bridged polycyclic systems. Preferred cycloalkyls have from 3 to 10 carbon atoms in their ring structure, and more preferably have 3, 4, 5, and 6 carbons in the ring structure. For example, "$C_{3-6}$ cycloalkyl" denotes such groups as cyclopropyl, cyclobutyl, cyclopentyl, or cyclohexyl.

As used herein, "cycloalkenyl" refers to ring-containing hydrocarbyl groups having at least one carbon-carbon double bond in the ring, and having from 4 to 12 carbons atoms.

As used herein, "cycloalkynyl" refers to ring-containing hydrocarbyl groups having at least one carbon-carbon triple bond in the ring, and having from 7 to 12 carbons atoms.

As used herein, "halo" or "halogen" refers to fluoro, chloro, bromo, and iodo. "Counterion" is used to represent a small, negatively charged species such as chloride, bromide, hydroxide, acetate, sulfate, tosylate, benezensulfonate, and the like.

As used herein, the term "heterocyclyl" or "heterocyclic" or "heterocycle" refers to a saturated, unsaturated or partially saturated, monocyclic, bicyclic or tricyclic ring (unless otherwise stated) containing 3 to 20 atoms of which 1, 2, 3, 4 or 5 ring atoms are chosen from nitrogen, sulphur or oxygen, which may, unless otherwise specified, be carbon or nitrogen linked, wherein a —CH$_2$— group is optionally be replaced by a —C(O)—; and where unless stated to the contrary a ring nitrogen or sulphur atom is optionally oxidised to form the N-oxide or S-oxide(s) or a ring nitrogen is optionally quarternized; wherein a ring —NH is optionally substituted by acetyl, formyl, methyl or mesyl; and a ring is optionally substituted by one or more halo. It is understood that when the total number of S and O atoms in the heterocyclyl exceeds 1, then these heteroatoms are not adjacent to one another. If the said heterocyclyl group is bi- or tricyclic then at least one of the rings may optionally be a heteroaromatic or aromatic ring provided that at least one of the rings is non-heteroaromatic. If the said heterocyclyl group is monocyclic then it must not be aromatic. Examples of heterocyclyls include, but are not limited to, piperidinyl, N-acetylpiperidinyl, N-methylpiperidinyl, N-formylpiperazinyl, N-mesylpiperazinyl, homopiperazinyl, piperazinyl, azetidinyl, oxetanyl, morpholinyl, tetrahydroisoquinolinyl, tetrahydroquinolinyl, indolinyl, tetrahydropyranyl, dihydro-2H-pyranyl, tetrahydrofuranyl and 2,5-dioxoimidazolidinyl.

As used herein, "heteroaryl" or "heteroaromatic" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl (i.e., pyridinyl), pyrimidinyl, pyrazinyl, pyridazinyl, triazinyl, furyl (i.e. furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, thiazolyl, benzothienyl, purinyl, carbazolyl, fluorenonyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 4 to about 14, 3 to about 7, or 5 to 6 ring-forming atoms. In some embodiments, the heteroaryl or heteroaromatic group has 1 to about 4, 1 to about 3, or 1 to 2 heteroatoms. In some embodiments, the heteroaryl or heteroaromatic group has 1 heteroatom.

As used herein, the phrase "protecting group" means temporary substituents which protect a potentially reactive functional group from undesired chemical transformations. Examples of such protecting groups include esters of carboxylic acids, silyl ethers of alcohols, and acetals and ketals of aldehydes and ketones respectively. The field of protecting group chemistry has been reviewed (Greene, T. W.; Wuts, P. G. M. *Protective Groups in Organic Synthesis*, 3$^{rd}$ ed.; Wiley: N.Y., 1999).

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric acid.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like diethyl ether, ethyl acetate, ethanol, isopropanol, or acetonitrile are used.

As used herein, "tautomer" means other structural isomers that exist in equilibrium resulting from the migration of a hydrogen atom. For example, keto-enol tautomerism where the resulting compound has the properties of both a ketone and an unsaturated alcohol.

As used herein "stable compound" and "stable structure" are meant to indicate a compound that is sufficiently robust to survive isolation to a useful degree of purity from a reaction mixture, and formulation into an efficacious therapeutic agent.

Compounds of the invention further include hydrates and solvates.

The present invention further includes isotopically-labeled compounds of the invention. An "isotopically" or "radiolabeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro receptor labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F $^{125}$I, $^{123}$I, $^{124}$I, $^{131}$I, $^{75}$Br, 76Br or $^{77}$Br will generally be most useful.

It is understood that a "radio-labeled compound" is a compound that has incorporated at least one radionuclide. In some embodiments the radionuclide is selected from the group consisting of $^3$H, 14C, $^{125}$I, $^{35}$S and $^{82}$Br.

The anti-dementia treatment defined herein may be applied as a sole therapy or may involve, in addition to the compound of the invention, conventional chemotherapy. Such chemotherapy may include one or more of the following categories of agents: acetyl cholinesterase inhibitors, anti-inflammatory agents, cognitive and/or memory enhancing agents or atypical antipsychotic agents.

Such conjoint treatment may be achieved by way of the simultaneous, sequential or separate dosing of the individual components of the treatment. Such combination products employ the compounds of this invention.

Compounds of the present invention may be administered orally, parenteral, buccal, vaginal, rectal, inhalation, insufflation, sublingually, intramuscularly, subcutaneously, topically, intranasally, intraperitoneally, intrathoracially, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient.

An effective amount of a compound of the present invention for use in therapy of dementia is an amount sufficient to symptomatically relieve in a warm-blooded animal, particularly a human the symptoms of dementia, to slow the progression of dementia, or to reduce in patients with symptoms of dementia the risk of getting worse.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or tablet disintegrating agents; it can also be an encapsulating material.

In powders, the carrier is a finely divided solid, which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers include magnesium carbonate, magnesium stearate, talc, lactose, sugar, pectin, dextrin, starch, tragacanth, methyl cellulose, sodium carboxymethyl cellulose, a low-melting wax, cocoa butter, and the like.

In some embodiments, the present invention provides a compound of formula I or a pharmaceutically acceptable salt thereof for the therapeutic treatment (including prophylactic treatment) of mammals including humans, it is normally formulated in accordance with standard pharmaceutical practice as a pharmaceutical composition.

In addition to the compounds of the present invention, the pharmaceutical composition of this invention may also contain, or be co-administered (simultaneously or sequentially) with, one or more pharmacological agents of value in treating one or more disease conditions referred to herein.

The term composition is intended to include the formulation of the active component or a pharmaceutically acceptable salt with a pharmaceutically acceptable carrier. For example this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

Liquid form compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. Liquid pharmaceutically administrable compositions can, for example, be prepared by dissolving, dispersing, etc, an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975.

The compounds of the invention may be derivatised in various ways. As used herein "derivatives" of the compounds includes salts (e.g. pharmaceutically acceptable salts), any complexes (e.g. inclusion complexes or clathrates with compounds such as cyclodextrins, or coordination complexes with metal ions such as $Mn^{2+}$ and $Zn^{2+}$), free acids or bases, polymorphic forms of the compounds, solvates (e.g. hydrates), prodrugs or lipids, coupling partners and protecting groups. By "prodrugs" is meant for example any compound that is converted in vivo into a biologically active compound.

Salts of the compounds of the invention are preferably physiologically well tolerated and non toxic. Many examples of salts are known to those skilled in the art. All such salts are within the scope of this invention, and references to compounds include the salt forms of the compounds.

Where the compounds contain an amine function, these may form quaternary ammonium salts, for example by reaction with an alkylating agent according to methods well known to the skilled person. Such quaternary ammonium compounds are within the scope of the invention.

Compounds containing an amine function may also form N-oxides. A reference herein to a compound that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, 1992. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Where the compounds contain chiral centres, all individual optical forms such as enantiomers, epimers and diastereoisomers, as well as racemic mixtures of the compounds are within the scope of the invention.

Compounds may exist in a number of different geometric isomeric, and tautomeric forms and references to compounds include all such forms. For the avoidance of doubt, where a compound can exist in one of several geometric isomeric or tautomeric forms and only one is specifically described or shown, all others are nevertheless embraced by the scope of this invention.

The quantity of the compound to be administered will vary for the patient being treated and will vary from about 100 ng/kg of body weight to 100 mg/kg of body weight per day and preferably will be from 10 pg/kg to 10 mg/kg per day. For instance, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention.

Compounds of the present invention have been shown to inhibit beta secretase (including BACE) activity in vitro. Inhibitors of beta secretase have been shown to be useful in blocking formation or aggregation of Aβ peptide and therefore have beneficial effects in treatment of Alzheimer's Disease and other neurodegenerative diseases associated with elevated levels and/or deposition of Aβ peptide. Therefore, it is believed that the compounds of the present invention may be used for the treatment of Alzheimer disease and disease associated with dementia. Hence, compounds of the present invention and their salts are expected to be active against age-related diseases such as Alzheimer, as well as other Aβ related pathologies such as Downs syndrome and β-amyloid angiopathy. It is expected that the compounds of the present invention would most likely be used as single agents but could also be used in combination with a broad range of cognition deficit enhancement agents.

Methods of Preparation

The present invention also relates to processes for preparing the compound of formula (I) as a free base or a pharmaceutically acceptable salt thereof. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in *Protective Groups in Organic Synthesis* by T. W. Greene, P. G. M. Wutz, 3rd Edition, Wiley-Interscience, N.Y., 1999. It is understood that microwaves can alternatively be used for the heating of reaction mixtures.

Another aspect of the present invention provides a process for preparing a compound of formula (I), or a pharmaceutically acceptable salt or an in vivo hydrolysable ester thereof, which process (wherein $R^1$, $R^2$, $R^3$, Z, Y, X, W and m, are, unless otherwise specified, as defined in formula (I)) comprises of:

(i) reacting a corresponding compound of formula (II):

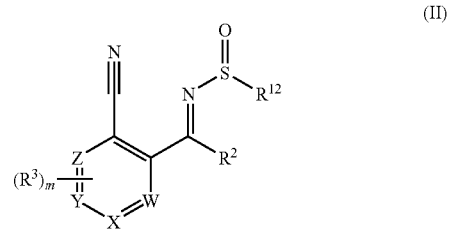

with an organometallic species of formula $M-R^1$ wherein M represents a metal such as lithium, or with for example a Grignard reagent, followed by cleavage of the nitrogen-sulfur bond. $R^{12}$ is commonly aryl or alkyl such as tert-butyl.

In process (i) a compound of formula (I) may be prepared by treating a compound of formula (II), with an appropriate organo metallic reagent of formula $M-R^1$ wherein M is a metal such as for example lithium or of the formula $L_nM-R^1$ such as for example an organo zinc reagent or a Grignard reagent, wherein L represents a ligand such as halogen and n is either 0 or more, followed by treatment with a suitable acid such as hydrochloric acid. The reaction may be performed in a suitable solvent such as diethyl ether or tetrahydrofuran at a temperature between −105° C. and room temperature.

(ia) A compound of formula (II) may be obtained by treating a compound of formula (IIa) with a compound of formula (IIb), wherein $R^{12}$ is commonly aryl or alkyl such as for example tert-butyl, under the influence of a suitable Lewis acid such as titanium (IV) ethoxide (Scheme 1). The reaction may be performed in a suitable solvent such as diethyl ether or tetrahydrofuran at a temperature between room temperature and reflux temperature.

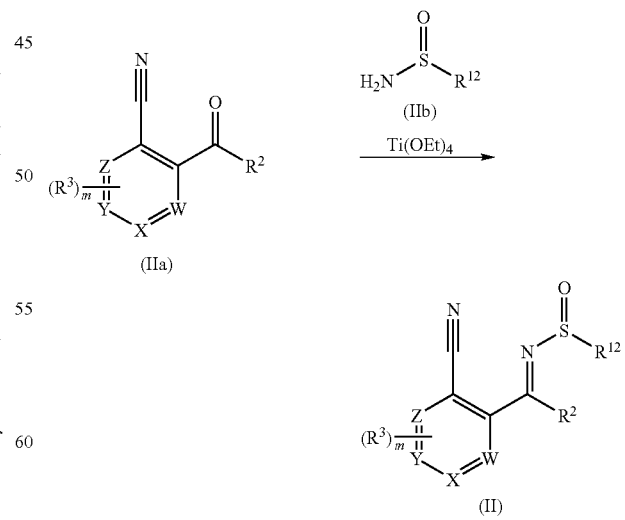

(ib) A compound of formula (IIa) may be obtained for example by metallation or halogen metal exchange of a compound of formula (IIe), wherein K is either a hydrogen or a halogen respectively, to obtain an intermediate of formula (IId), wherein L is a ligand such as halogen and n is between 0 and 6, which is not isolated but reacted further with a compound of formula (IIc), wherein LG is either N(CH$_3$) (OCH$_3$) or halogen or another suitable leaving group (Scheme 2) as for example described by R. K. Dieter, (*Tetrahedron*, 55 (1999) 4177-4236).

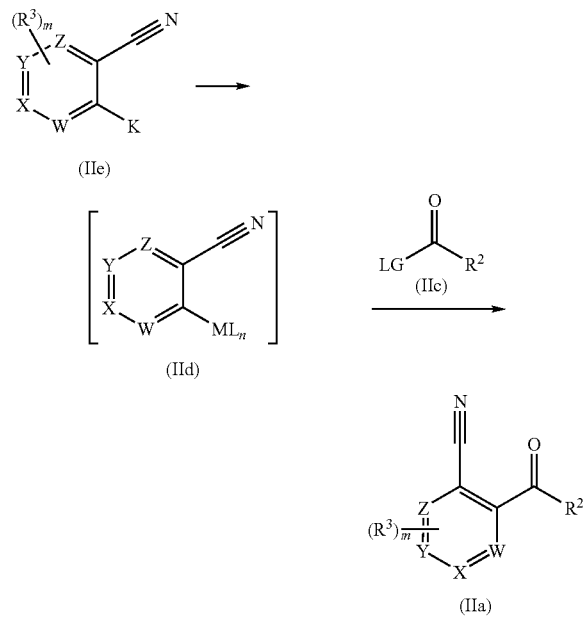

The reaction may be carried out by treating a compound of formula (IIe) wherein K is a halogen such as iodine or bromine with an appropriate metallating reagent such as an alkyllithium such as tert-butyllithium or n-butyllithium or isopropylmagnesium bromide, magnesium, zinc or manganese, by standard methods known in the art, and optionally if appropriate further transmetallating the formed intermediate by treatment with a metal salt or metal complex, for example such as coppercyanide dilithiumbromide, to obtain a new intermediate of formula (IId), and then treat the intermediate (IId) with a compound of formula (IIc) wherein LG e.g. is halogen such as chlorine or N(CH$_3$)(OCH$_3$), optionally if appropriate this transformation may be performed under the influence of a transition metal catalyst such as a palladium salt or complex as for example described in the above reference. The reaction may be performed in a suitable solvent such as diethyl ether or tetrahydrofuran at a temperature between −105° C. and room temperature.

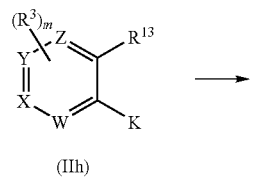

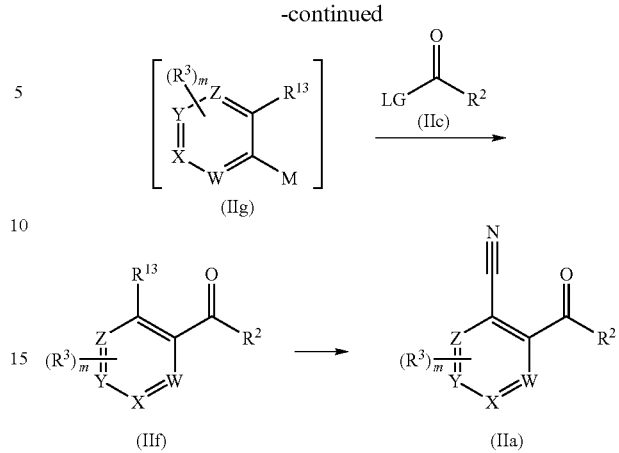

Alternatively, a method to obtain a compound of formula (IIa) is by reacting a compound of formula (IIh) wherein R$^{13}$ is halogen, CONH$_2$ or COOR$^{14}$, wherein R$^{14}$ is hydrogen or alkyl, in the same manner as described above for conversion of (IIe) to (IIa) to obtain a compound of formula (IIf), wherein R$^{13}$ is as specified above, and then transform a compound of formula (IIf) into (IIa) by known methods described in for example *Advanced Organic Chemistry* by Jerry March 4$^{th}$ edition, Wiley Interscience, 1992 (Scheme 3).

(ii) In the case that at least one R$^4$ is aryl or heteroaryl, an alternative method of preparing a compound of formula (I) consists of attaching R$^4$ to R$^1$ and/or R$^2$ via a metal catalyzed cross-coupling reaction, starting for example from a compound of formula (Ia):

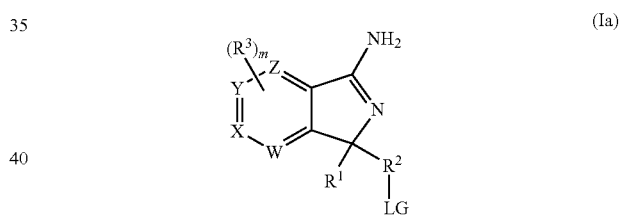

wherein LG represents a leaving group such as halogen such as chlorine, bromine or iodine or an alkyl-, aryl- or haloalkyl-sulfonate such as triflate, and reacting it with a compound of formula T-R$^4$ which represents an aryl- or heteroaryl-boronic acid or ester or stannane and R$^4$ is defined above, under the influence of a transition metal catalyst as for example described in *Metal Catalyzed Cross-coupling Reactions* by F. Diederich and P. J. Stang, Wiley VCH, Weinheim, 1998.

In process (ii), the reaction may be carried out by coupling of a suitable compound such as a compound of formula (Ia) with an appropriate aryl boronic acid or ester or stannane. The reaction may be carried out using a suitable palladium catalyst such as, [1,1'-bis(diphenylphosphino)ferrocene]palladium(II) chloride, tetrakis(triphenylphosphine)-palladium (0), palladium diphenylphosphineferrocene dichloride, palladium(II) acetate or bis(dibenzylideneacetone) palladium (0), together with, or without, a suitable ligand such as triphenylphosphine, tri-tert-butylphosphine or 2-(dicyclohexylphosphino)biphenyl, or using a nickel catalyst such as nickel on charcoal or 1,2-bis(diphenylphosphino)ethanenickel dichloride together with zinc and sodium triphenylphosphinetrimetasulfonate. A suitable base such as cesium fluoride, an alkyl amine such as triethyl amine, or an alkali metal or alkaline earth metal carbonate or hydroxide such as potassium carbonate, sodium carbonate, cesium carbonate, or sodium hydroxide may be used in the reaction, which may be performed in a temperature range between +20° C. and +160° C., in a suitable solvent such as toluene, tetrahydrofuran, dioxane, dimethoxyethane, water, ethanol or N,N-dimethylformamide, or mixtures thereof.

Compounds of formula (IIb), (IIc), (IIe), (IIh) and T-R$^4$ are commercially available compounds, or they are known in the literature, or they are prepared by standard processes known in the art.

General Methods

Starting materials used were available from commercial sources, or prepared according to literature procedures.

$^1$H NMR spectra were recorded in the indicated deuterated solvent, using a Bruker DPX400 NMR spectrometer operating at 400 MHz for $^1$H equipped with a 4-nucleus probehead with Z-gradients or a Bruker av400 NMR spectrometer operating at 400 MHz $^1$H equipped with a 3 mm flow injection SEI $^1$H/D-$^{13}$C probehead with Z-gradients, using a BEST 215 liquid handler for sample injection. Chemical shifts are given in ppm. Resonance multiplicities are denoted s, d, t, q, m and br for singlet, doublet, triplet, quartet, multiplet, and broad respectively.

LC-MS analyses were performed on a LC-MS system consisting of a Waters Alliance 2795HPLC, a Waters PDA 2996 diode array detector, a Sedex 75 ELS detector and a ZQ single quadrupole mass spectrometer. The mass spectrometer was equipped with an electrospray ion source (ES) operated in positive or negative ion mode. The capillary voltage was set to 3.2 kV and the cone voltage to 30 V, respectively. The mass spectrometer was scanned between m/z 100-700 with a scan time of 0.3s. The diode array detector scanned from 200-400 nm. The temperature of the ELS detector was adjusted to 40° C. and the pressure was set to 1.9 bar. Separation was performed on an X-Terra MS C8, 3.0 mm×50 mm, 3.5 μm (Waters) run at a flow rate of 1 mL/min. A linear gradient was applied starting at 100% A (A: 10 mM ammonium acetate in 5% acetonitrile or 8 mM formic acid in 5% acetonitrile) ending at 100% B (B: acetonitrile). The column oven temperature was set to 40° C., or LC-MS analyses were performed on a LC-MS consisting of a Waters sample manager 2777C, a Waters 1525 μ binary pump, a Waters 1500 column oven, a Waters ZQ single quadrupole mass spectrometer, a Waters PDA2996 diode array detector and a Sedex 85 ELS detector. The mass spectrometer was equipped with an electrospray ion source (ES) operated in positive or negative ion mode. The mass spectrometer scanned between m/z 100-700 with a scan time of 0.3s. The capillary voltage was set to 3.4 kV and the cone voltage was set to 30 V, respectively. The diode array detector scanned from 200-400 nm. The temperature of the ELS detector was adjusted to 40° C. and the pressure was set to 1.9 bar. For separation a linear gradient was applied starting at 100% A (A: 10 mM ammonium acetate in 5% acetonitrile or 8 mM formic acid in 5% acetonitrile) and ending at 100% B (B: acetonitrile). The column used was a Gemini C18, 3.0 mm×50 mm, 3 μm, (Phenomenex) which was run at a flow rate of 1 ml/min. The column oven temperature was set to 40° C.

GC-MS: Compound identification was performed on a GC-MS system (GC 6890, 5973N MSD) supplied by Agilent Technologies. The column used was a VF-5 MS, ID 0.25 mm×15m, 0.25 μm (Varian Inc.). A linear temperature gradient was applied starting at 40° C. (hold 1 min) and ending at 300° C. (hold 1 min), 25° C./minute. The mass spectrometer was equipped with a chemial ionisation (CI) ion source and the reactant gas was methane. The mass spectrometer was equipped with an electron impact (EI) ion source and the electron voltage was set to 70 eV. The mass spectrometer scanned between m/z 50-500 and the scan speed was set to 3.25 scan/s, or Compound identification was performed on a GC-MS system (GC 6890, 5973N MSD) supplied by Agilent Technologies. The mass spectrometer was equipped with a Direct Inlet Probe (DIP) interface manufactured by SIM GmbH. The mass spectrometer was configured with a chemical ionisation (CI) ion source and the reactant gas was methane. The mass spectrometer was equipped with an electron impact (EI) ion source and the electron voltage was set to 70 eV. The mass spectrometer scanned between m/z 50-500 and the scan speed was set to 3.25 scan/s. A linear temperature gradient was applied starting at 40° C. (hold 1 min) and ending at 300° C. (hold 1 min), 25° C./minute. The column used was a VF-5 MS, ID 0.25 mm×30m, 0.25 μm (Varian Inc.).

Preparative-HPLC: Preparative chromatography was run on Waters auto purification HPLC with a diode array detector. Column: XTerra MS C8, 19×300 mm, 10 μm. Gradient with acetonitrile/0.1M ammonium acetate in 5% acetonitrile in MilliQ Water. Flow rate: 20 mL/min. Alternatively, purification was achieved on a semi preparative Shimadzu LC-8A HPLC with a Shimadzu SPD-10A UV-vis.-detector equipped with a Waters Symmetry® column (C 18, 5 μm, 100 mm×19 mm). Gradient with acetonitrile/0.1% trifluoroacetic acid in MilliQ Water. Flow rate: 10 mL/min. Alternatively, another column was used; Atlantis C18 19×100 mm, 5 μm column. Gradient with acetonitrile/0.1 M ammonium acetate in 5% acetonitrile in MilliQ Water. Flow rate: 15 mL/min.

Microwave heating was performed in a Creator or Initiaror or Smith Synthesizer Single-mode microwave cavity producing continuous irradiation at 2450 MHz.

Thin layer chromatography (TLC) was performed on Merch TLC-plates (Silica gel 60 F$_{254}$) and UV visualized the spots. Column chromatography was performed on a Combi Flash® Companion™ using RediSep™ normal-phase flash columns or using Merck Silica gel 60 (0.040-0.063 mm).

Compounds have been named using either ACD/Name, version 9.0, software from Advanced Chemistry Development, Inc. (ACD/Labs), Toronto ON, Canada, www.acdlabs.com, 2005, or Lexichem, version 1.4, software from OpenEye.

The following abbreviations have been used:
h hour(s)
THF tetrahydrofuran

EXAMPLES

Below follows a number of non-limiting examples of compounds of the invention.

Example 1

3-(3-Bromobenzoyl)pyridine-2-carbonitrile

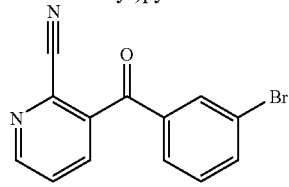

A suspension of highly active zinc (Rieke zinc) in THF (100 mg/mL, 12.7 mL, 19.4 mmol) was added via a syringe to a solution of 3-bromo-2-cyanopyridine (1.189 g, 6.497 mmol) in anhydrous THF (20 mL) under an atmosphere of argon. The mixture was stirred for four h at room temperature and then at 50° C. for 15 min. The remaining zinc powder was allowed to settle at the bottom of the flask overnight at −20° C. The top solution was transferred to another flask and cooled to −20° C. To this was added a 1 M solution of copper cyanide di(lithium bromide) complex in THF (6.82 mL) and the resulting mixture was stirred for 5 min at −20° C. and for 35 min at 0° C. and then cooled to −30° C. prior to the addition of 3-bromobenzoyl chloride (1.78 g, 8.12 mmol). The mixture was stirred for 6 h during which time the temperature went from −30° C. to 0° C. The reaction was quenched by the addition of saturated ammonium chloride solution and ethyl acetate was added. The phases were separated and the organic phase was washed with 1 M sodium carbonate solution and with brine. The solution was dried over magnesium sulfate and evaporated. Purification by column chromatography using a gradient of increasing concentration of ethyl acetate in heptane (0-50%) gave 1.18 g (63% yield) of the title compound. $^1$H NMR (CDCl$_3$) δ 8.92 (dd, 1H), 7.98 (dd, 1H), 7.96 (t, 1H), 7.84-7.81 (m, 1H), 7.73-7.70 (m, 1H), 7.68 (dd, 1H), 7.43 (t, 1H); MS (CI) m/z M$^+$ 287, 289.

Example 2

N-[(1E)-(3-Bromophenyl)(2-cyanopyridin-3-yl)methylene]-2-methylpropane-2-sulfinamide

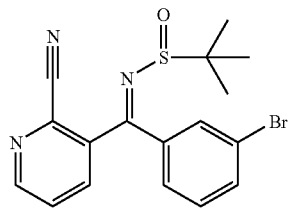

Titanium(IV)ethoxide (1 M solution in THF, 18.7 mL) was added to a solution of 3-(3-bromobenzoyl)pyridine-2-carbonitrile (2.680 g, 9.334 mmol) and tert-butylsulfinamide (1.244 g, 10.27 mmol) in anhydrous THF (10 mL) under an atmosphere of argon. The mixture was heated at 50° C. for 70 h. After cooling to room temperature the mixture was diluted with methanol (20 mL) and 100 drops of water was added. The resulting mixture was allowed to stand for about 1 h and then filtered through a pad of sodium sulfate. The filter cake was taken up in saturated aqueous sodium hydrogen carbonate solution and dichloromethane. The mixture was stirred over night, the phases were separated and the aqueous phase was extracted with dichloromethane. The extracts were combined with the filtrate from above, dried over sodium sulfate and evaporated. Purification by column chromatography using a gradient of increasing concentration of acetonitrile in dichloromethane (0-20%) gave 2.52 g (69% yield) of the title compound. $^1$H NMR (CDCl$_3$) δ 8.81 (d, 1H), 7.76 (m, 2H), 7.68 (m, 1H), 7.62 (dd, 1H), 7.43 (d, 1H), 7.32 (t, 1H), 1.39 (br. s., 9H).

Example 3

5-(3-Bromophenyl)-5-(4-methoxyphenyl)-5H-pyrrolo[3,4-b]pyridin-7-amine

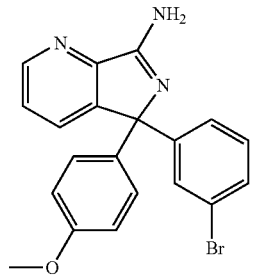

Butyllithium (2.5 M in hexanes, 0.947 mL) was added dropwise to a solution of 4-bromoanisole (483 mg, 2.58 mmol) in anhydrous THF at −78° C. under an atmosphere of argon. The mixture was stirred at that temperature for 30 min and then a solution of N-[(1E)-(3-bromophenyl)(2-cyanopyridin-3-yl)methylene]-2-methypropane-2-sulfinamide (Example 2, 840 mg, 2.15 mmol) in THF (10 mL) was added dropwise. Stirring was continued for 3 h at −78° C., and then for 1 h at −25° C. The reaction was quenched by the addition of water, the mixture was diluted with ethyl acetate and washed with water, dried over magnesium sulfate and concentrated. The residue was dissolved in methanol (20 mL) and to this was added 2 M hydrochloric acid in diethyl ether (2.5 mL). The mixture was stirred at room temperature for 22 h and then concentrated. The residue was partitioned between dichloromethane and saturated aqueous sodium hydrogen carbonate, dried over sodium sulfate and concentrated. Purification by column chromatography using a gradient of increasing concentration of ethyl acetate in dichloromethane (0-50%) and finally 5% of 2 M ammonia in methanol in ethyl acetate-dichloromethane (45:50) gave 115 mg (14% yield) of the title compound. $^1$H NMR (CDCl$_3$) δ 8.62 (dd, 1H), 7.88 (dd, 1H), 7.46 (t, 1H), 7.37 (m, 2H), 7.26 (m, 1H), 7.21 (m, 2H), 7.14 (t, 1H), 6.81 (m, 2H), 3.78 (s, 3H); MS (ESI) m/z 394, 396 [M+1]$^+$.

Example 4

5-(3-Bromophenyl)-5-pyridin-4-yl-5H-pyrrolo[3,4-b]pyridin-7-amine

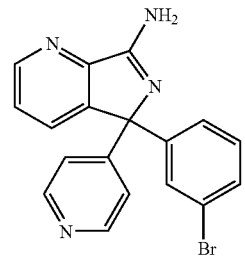

tert-Butyllithium (1.5 M solution in pentane, 2.15 mL) was diluted with anhydrous THF (10 mL) at −100° C. under an atmosphere of argon. To this was added dropwise a solution of 4-iodopyridine (330 mg, 1.773 mmol) in anhydrous THF (8 ml,), the mixture was stirred at −100° C. for 5 min and then a solution of N-[(1E)-(3-bromophenyl)(2-cyanopyridin-3-yl) methylene]-2-methylpropane-2-sulfinamide (Example 2, 629 mg, 1.612 mmol) in THF (10 mL) was added dropwise while maintaining the temperature at or below −100° C. The mixture was stirred for 1.5 h during which time it was allowed to warm up to −75° C. The reaction was quenched by the addition of water and the mixture was diluted with ethyl acetate. The phases were separated and the aqueous phase was extracted with ethyl acetate. The combined extracts were washed with saturated aqueous sodium hydrogen carbonate and brine, then dried over magnesium sulfate and evaporated. The residue was dissolved in methanol (10 mL) and treated with 2 M hydrochloric acid in diethyl ether overnight at room temperature. The solvents were evaporated and the residue was taken up with saturated aqueous hydrogen carbonate and dichloromethane. The phases were separated, the aqueous phase was extracted with ethyl acetate. The combined organic phases were dried over sodium sulfate and evaporated. Purification by column chromatography using a gradient of increasing concentration of 2 M methanolic ammonia in dichloromethane (from 0 to 5%) gave 406 mg (69% yield) of the title compound. $^1$H NMR (CDCl$_3$) δ 8.67 (dd, 1H), 8.53

(m, 2H), 7.90 (dd, 1H), 7.41 (m, 3H), 7.23 (m, 3H), 7.18 (m, 1H); MS (ESI) m/z 365, 367 [M+1]+.

Example 5

5-(4-Methoxyphenyl)-5-(3 -pyrimidin-5-ylphenyl)-5H-pyrrolo[3,4-b]pyridin-7-amine

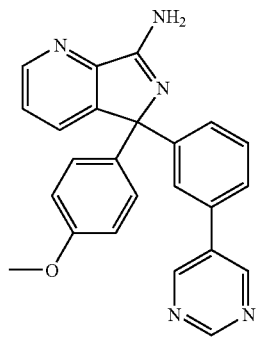

A mixture of 5-(3-bromophenyl)-5-(4-methoxyphenyl)-5H-pyrrolo[3,4-b]pyridin-7-amine (Example 3, 85 mg, 0.215 mmol), pyrimidin-5-ylboronic acid (35 mg, 0.280 mmol), [1,1'-bis(diphenylphosphino)ferrocene]palladium(II) dichloride dichloromethane adduct (18 mg, 0.022 mmol) and cesium carbonate (210 mg, 0.645 mmol) in a mixture of 1,2-dimethoxyethane, water and ethanol (6:3:1, 5 mL) was heated by microwave irradiation at 130° C., under an argon atmosphere for 15 min. After cooling to ambient temperature the mixture was filtered, concentrated in vacuo and purified by preparative HPLC to give 22 mg (26% yield) after liberating the free base by treatment of the acetate with sodium hydrogen carbonate. $^1$H NMR (CDCl$_3$) δ 9.17 (s, 1H), 8.86 (s, 2H), 8.63 (dd, 1H), 7.92 (dd, 1H), 7.55 (m, 1H), 7.48-7.40 (m, 3H), 7.36 (dd, 1H), 7.26 (m, 2H), 6.82 (m, 2H), 3.78 (s, 3H); MS (ESI) m/z 394 [M+1]+.

Examples 6-12

Using an analogous procedure to that described in Example 5, the appropriate bromophenylpyrrolopyridinamine derivative was reacted with the appropriate boronic acid or ester to give the compounds Example 6-12 described in Table 1.

TABLE I

| Ex | Chemical name | R$^4$ | R$^2$ | m/z [M + 1]+ | $^1$H-NMR (CDCl$_3$) ppm |
|---|---|---|---|---|---|
| 6 | 5-[3-(2-Fluoropyridin-3-yl)phenyl]-5-(4-methoxyphenyl)-5H-pyrrolo[3,4-b]pyridin-7-amine | | | 411 | 8.61 (dd, 1 H), 8.16 (m, 1 H), 7.93 (dd, 1 H), 7.80 (m, 1 H), 7.53 (m, 1 H), 7.48-7.34 (m, 4 H), 7.28-7.21 (m, 3 H), 6.81 (m, 2 H), 3.77 (s, 3 H). |
| 7 | 5-(4-Methoxyphenyl)-5-[3-(5-methoxypyridin-3-yl)phenyl]-5H-pyrrolo[3,4-b]pyridin-7-amine | | | 423 | δ 8.62 (dd, 1 H), 8.36 (d, 1 H), 8.26 (d, 1 H), 7.92 (dd, 1 H), 7.55 (m, 1 H), 7.47-7.44 (m, 1 H), 7.39-7.33 (m, 3 H), 7.29 (m, 1 H), 7.26 (m, 2 H), 6.81 (m, 2 H), 3.89 (s, 3 H), 3.78 (s, 3 H). |
| 8 | 5-(4-Methoxyphenyl)-5-(3-pyridin-3-ylphenyl)-5H-pyrrolo[3,4-b]pyridin-7-amine | | | 393 | δ 8.75 (m, 1 H), 8.61 (dd, 1 H), 8.55 (dd, 1 H), 7.92 (dd, 1 H), 7.79 (m, 1 H) 7.55 (m, 1 H), 7.46 (m, 1 H) 7.34 (m, 4 H), 7.26 (m, 2 H) 6.81 (m, 2 H), 3.78 (s, 3 H). |

TABLE I-continued

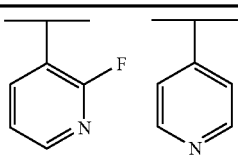

| Ex | Chemical name | R⁴ | R² | m/z [M + 1]⁺ | ¹H-NMR (CDCl₃) ppm |
|---|---|---|---|---|---|
| 9 | 5-[3-(2-Fluoropyridin-3-yl)phenyl]-5-pyridin-4-yl-5H-pyrrolo[3,4-b]pyridin-7-amine |  | 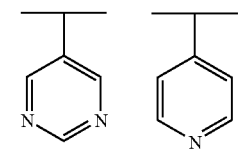 | 382 | δ 8.67 (dd, J = 4.80, 1.26 Hz, 1 H), 8.47 (m, 2 H), 8.39 (dd, 1 H), 8.22 (m, 1 H), 8.02 (m, 1 H), 7.57 (m, 1 H), 7.53-7.42 (m, 5 H), 7.35 (m, 2 H), 6.95 (br. s., 2 H). |
| 10 | 5-Pyridin-4-yl-5-(3-pyrimidin-5-ylphenyl)-5H-pyrrolo[3,4-b]pyridin-7-amine |  | 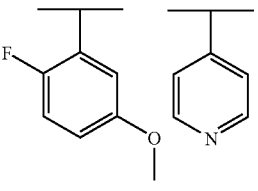 | 365 | 9.18 (s, 1 H), 8.86 (s, 2 H), 8.67 (dd, J = 4.93, 1.39 Hz, 1 H), 8.54 (m, 2 H) 7.94 (dd, J = 7.71, 1.39 Hz, 1 H), 7.49 (m, 3 H), 7.39 (m, 2 H), 7.27 (m, 2 H). |
| 11 | 5-(2'-Fluoro-5-methoxybiphenyl-3-yl)-5-pyridin-4-yl-5H-pyrrolo[3,4-b]pyridin-7-amine 0.25 acetate |  | 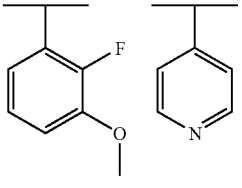 | 411 | 8.67 (dd, 1 H), 8.53 (m, 2 H), 7.95 (dd, 1 H), 7.47 (m, 2 H), 7.40 (m, 2 H), 7.32 (m, 1 H), 7.27 (m, 2 H), 7.03 (m, 1 H), 6.88 (m, 1 H), 6.81 (m, 1 H), 3.80 (s, 3 H), 2.07 (s, 0.75 H). |
| 12 | 5-(2'-Fluoro-3'-methoxybiphenyl-3-yl)-5-pyridin-4-yl-5H-pyrrolo[3,4-b]pyridin-7-amine 0.5 acetate |  | 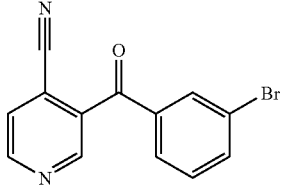 | 411 | 8.67 (dd, 1 H), 8.53 (m, 2 H), 7.96 (dd, 1 H), 7.44 (m, 4 H), 7.33 (m, 1 H), 7.27 (m, 2 H), 7.10 (m, 1 H), 6.94 (m, 2 H), 3.92 (s, 3 H), 2.07 (s, 1.5 H). |

Example 13

3-(3-Bromobenzoyl)pyridine-4-carbonitrile

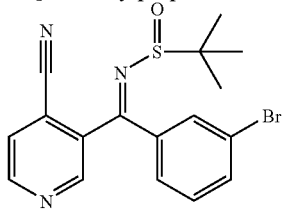

A suspension of highly active zinc (Rieke zinc) in THF (100 mg/mL, 33 mL, 50 mmol) was added via a syringe to a solution of 3-bromo-4-cyanopyridine (3.02 g, 16.5 mmol) in anhydrous THF (100 mL) under an atmosphere of argon. The mixture was stirred for 3 h at 50° C. and then the excess zinc powder was allowed to settle at −20° C. for 2 days. The top solution was transferred to another flask and cooled to −20° C., to this was added a 1 M solution of copper cyanide dilithium bromide complex in THF (17.3 mL) and the resulting mixture was stirred for 5 min at −20° C. and for 30 min at 0° C. and then cooled to −30° C. prior to the addition of 3-bromobenzoyl chloride (1.78 g, 8.12 mmol). The mixture was stirred for 16 h during which time the temperature went from −30° C. to room temperature. The reaction was quenched by the addition of saturated ammonium chloride solution and the mixture was extracted with ethyl acetate. The combined organic phases were washed with 1 M sodium carbonate solution, dried over magnesium sulfate and evaporated. Purification by column chromatography using a gradient of increasing concentration of ethyl acetate in heptane (0-50%) gave 2.1 g of a mixture of different species containing the title compound. MS (CI) m/z 287, 289 [M+1]⁺.

Example 14

N-[(1E)-(3-Bromophenyl)(4-cyanopyridin-3-yl)methylene]-2-methylpropane-2-sulfinamide The title compound was prepared as described in Example 2 starting with a mixture containing 3-(3-bromobenzoyl)pyridine-4-carbonitrile. $^1$H NMR (CDCl$_3$) δ 8.88 (m, 1H), 8.70 (br s, 1H), 7.75 (br. s., 1H), 7.68 (m, 1H), 7.63 (m, 1H), 7.43 (m, 1H), 7.33 (br s, 9H).

Example 15

3-(3-Bromophenyl)-3-pyridin-4-yl-3H-pyrrolo[3,4-c]pyridin-1-amine

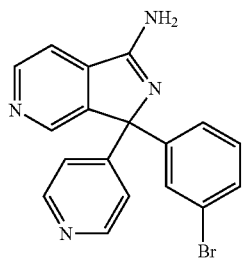

The title compound was made in 62% yield as described in Example 4 starting from N-[(1E)-(3-bromophenyl)(4-cyanopyridin-3-yl)methylene]-2-methylpropane-2-sulfinamide (Example 14). $^1$H NMR (DMSO-d$_6$) δ 9.17 (d, 1H), 8.73 (d, 1H), 8.47 (m, 2H), 7.83 (dd, 1H), 7.50 (t, 1H), 7.46 (m, 1H), 7.40 (m, 1H), 7.33 (m, 2H), 7.28 (t, 1H), 7.21 (br. s., 2H).

Examples 16-17

Using an analogous procedure to that described in Example 5, 3-(3-bromophenyl)-3-pyridin-4-yl-3H-pyrrolo[3,4-c]pyridin-1-amine was reacted with the appropriate boronic acid or ester to give the compounds Example 16-17 described in Table II.

Example 18

N-[(1E)-(3-Bromophenyl)(4-cyanopyridin-3-yl)methylene]-2-methylpropane-2-sulfinamide

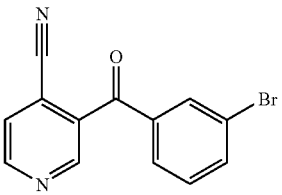

A solution of isopropylmagnesium bromide (1M in tetrahydrofuran, 5.27 ml, 5.27 mmol) was added to a solution of 2-iodonicotinonitrile (1.102 g, 4.79 mmol) in anhydrous tetrahydrofuran (20 mL) at −60° C. under an atmosphere of argon. The mixture was stirred for 30 minutes while the temperature was kept between −60 and −40° C. The mixture was then cooled to −78° and added to a cooled (−78° C.) solution of 3-bromobenzoyl chloride (2.103 g, 9.58 mmol) in anhydrous tetrahydrofuran (20 mL). The resulting mixture was stirred over night as the temperature was allowed to slowly increase to room temperature. The reaction was quenched by the addition of water, and the mixture was extracted with ethyl acetate, the combined extracts were dried over magnesium sulfate and evaporated. The residue was purified by flash chromatography, using a gradient of ethyl acetate in heptane (0-50%) to give 1.140 g (83% yield) of the title compound. MS (CI) m/z 287, 289 [M+1]$^+$.

TABLE II

| Ex | Chemical name | R$^4$ | R$^2$ | m/z [M + 1]$^+$ | $^1$H-NMR (DMSO-d$_6$) ppm |
|---|---|---|---|---|---|
| 16 | 3-Pyridin-4-yl-3-(3-pyrimidin-5-ylphenyl)-3H-pyrrolo[3,4-c]pyridin-1-amine | pyrimidin-5-yl | pyridin-4-yl | 411 | 9.31 (s, 1 H), 9.18 (s, 1 H), 9.04 (s, 2 H), 8.72 (d, 1 H), 8.47 (m, 2 H), 7.82 (dd, 1 H), 7.73 (t, 1 H), 7.68 (m, 1 H), 7.55 (m, 1 H), 7.48 (t, 1 H), 7.38 (m, 2 H). |
| 17 | 3-[3-(2-Fluoropyridin-3-yl)phenyl]-3-pyridin-4-yl-3H-pyrrolo[3,4-c]pyridin-1-amine | 2-fluoropyridin-3-yl | pyridin-4-yl | 423 | 9.20 (d, 1 H), 8.72 (d, 1 H), 8.47 (m, 2 H), 8.22 (m, 1 H), 8.03 (m, 1 H), 7.83 (dd, 1 H), 7.59 (m, 1 H), 7.47 (m, 4 H), 7.37 (m, 2 H) 7.18 (br s, 2 H). |

Example 19

N-[(1E)-(3-Bromophenyl)(3-cyanopyridin-2-yl)methylene]-2-methylpropane-2-sulfinamide

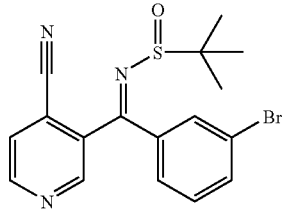

The title compound was prepared in 27% yield by an analogous procedure to that described in Example 2 by using N-[(1E)-(3-bromophenyl)(4-cyanopyridin-3-yl)methylene]-2-methylpropane-2-sulfinamide as starting material. $^1$H NMR (DMSO-$d_6$) δ 8.91 (dd, 1H), 8.46 (dd, 1H), 7.84 (m, 1H), 7.73 (dd, 1H), 7.66 (m, 1H), 7.46 (m, 2H), 3.32 (s, 3H), 1.28 (s, 9H).

Example 20

7-(3-Bromophenyl)-7-pyridin-4-yl-7H-pyrrolo[3,4-b]pyridin-5-amine

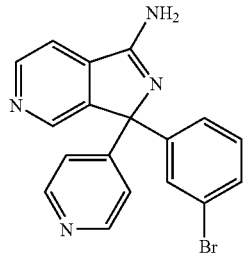

The title compound was prepared in 63% yield by an analogous procedure to that described in Example 4 by using N-[(1E)-(3-bromophenyl)(3-cyanopyridin-2-yl)methylene]-2-methylpropane-2-sulfinamide as starting material. $^1$H NMR (DMSO-$d_6$) δ 8.70 (dd, 1H), 8.46 (m, 2H), 8.18 (dd, 1H), 7.75 (t, 1H), 7.65 (m, 1H), 7.52 (dd, 1H), 7.49 (m, 2H), 7.43 (m, 1H), 7.27 (t, 1H), 7.15 (br s, 2H); MS (ES) m/z 365, 367 [M+1]$^+$.

Examples 21-23

Using an analogous procedure to that described in Example 5, 7-(3-bromophenyl)-7-pyridin-4-yl-7H-pyrrolo[3,4-b]pyridin-5-amine was reacted with the appropriate boronic acid or ester to give the compounds in Example 21-23 described in Table III.

TABLE III

| Ex | Chemical name | R$^4$ | R$^2$ | m/z [M + 1]$^+$ | $^1$H-NMR (DMSO-$d_6$) ppm |
|----|---------------|-------|-------|-----------------|------------------------------|
| 21 | 7-[3-(2-Fluoropyridin-3-yl)phenyl]-7-pyridin-4-yl-7H-pyrrolo[3,4-b]pyridin-5-amine | 2-fluoropyridin-3-yl | pyridin-4-yl | 382 | 8.69 (dd, 1 H) 8.46 (m, 2 H) 8.23 (m, 1 H) 8.19 (dd, 1 H) 7.99 (m, 1 H) 7.86 (m, 1 H) 7.71 (m, 1 H) 7.55 (m, 2 H) 7.51 (dd, 1 H) 7.45 (m, 3 H) 7.13 (br s, 2 H) |
| 22 | 7-Pyridin-4-yl-7-(3-pyrimidin-5-ylphenyl)-7H-pyrrolo[3,4-b]pyridin-5-amine | pyrimidin-5-yl | pyridin-4-yl | 365 | 9.18 (s, 1 H) 8.97 (s, 2 H) 8.71 (dd, 1 H) 8.45 (m, 2 H) 8.18 (dd, 1 H) 7.96 (t, 1 H) 7.77 (m, 1 H) 7.64 (m, 1 H) 7.56 (m, 2 H) 7.51 (dd, 1 H) 7.47 (t, 1 H) 7.12 (br s, 2 H) |
| 23 | 7-(2-Fluoro-3'-methoxybiphenyl-3-yl)-7-pyridin-4-yl-7H-pyrrolo[3,4-b]pyridin-5-amine | 2-fluoro-3-methoxyphenyl | pyridin-4-yl | 411 | 8.68 (dd, 1 H) 8.45 (m, 2 H) 8.17 (dd, 1 H) 7.78 (m, 1 H) 7.64 (m, 1 H) 7.56 (m, 2 H) 7.50 (dd, 1 H) 7.38 (m, 2 H) 7.16 (m, 2 H) 7.09 (br s, 2 H) 6.91 (m, 1 H) 3.85 (s, 3 H) |

Assays

Compounds were tested in at least one of the following assays:

β-Secretase Enzyme

The enzyme used in the IGEN Cleavage-, Fluorescent-, TR-FRET- and BiaCore assays is described as follows:

The soluble part of the human β-Secretase (AA1-AA460) was cloned into the ASP2-Fc10-1-IRES-GFP-neoK mammalian expression vector. The gene was fused to the Fc domain of IgG1 (affinity tag) and stably cloned into HEK 293 cells. Purified sBACE-Fc is stored in Tris buffer, pH 9.2 and has a purity of 95%.

IGEN Cleavage Assay

The enzyme was diluted to 43 μg/ml in 40 mM MES pH 5.0. The IGEN substrate was diluted to 12 μM in 40 mM MES pH 5.0. Compounds were diluted to the desired concentration in dimethyl sulfoxide (final dimethyl sulfoxide concentration in assay is 5%). The assay was performed in a 96 well PCR plate from Greiner (#650201). Compound in dimethyl sulfoxide (3 μL) and enzyme (27 μL) were added to the plate, and pre-incubated for 10 min. The reaction was started with substrate (30 μL). The final dilution of enzyme was 20 μg/ml and the final concentration of substrate was 6 μM. After 20 minutes reaction at room temperature (RT), the reaction was stopped by removing 10 μL of the reaction mix and diluting it 1:25 in 0.2 M Trizma-HCl, pH 8.0. The product was quantified by adding 50 μL of a 1:5000 dilution of the neoepitope antibody to 50 μL of the 1:25 dilution of the reaction mix (all antibodies and the streptavidin coated beads were diluted in PBS containing 0.5% BSA and 0.5% Tween20). Then, 100 μL of 0.2 mg/mL streptavidin coated beads (Dynabeads M-280) and a 1:5000 dilution of ruthenylated goat anti-rabbit (Ru-GαR) antibody was added. The mixture was measured for electro-chemiluminescence in a BioVeris M8 Analyzer after 2 hours of incubation with shaking at RT. The dimethyl sulfoxide control defined 100% activity level and 0% activity was defined by exclusion of the enzyme (using 40 mM MES pH 5.0 buffer instead).

Fluorescent Assay

The enzyme was diluted to 52 μg/ml in 40 mM MES pH 5.0. The substrate (Dabcyl-Edans) was diluted to 30 μM in 40 mM MES pH 5.0. Compounds were diluted to the desired concentration in dimethyl sulfoxide (final dimethyl sulfoxide concentration in assay is 5%). The assay is done in a Corning 384 well round bottom, low volume, non-binding surface plate (Corning #3676). Enzyme (9 μL) together with 1 μL of compound in dimethyl sulfoxide were added to the plate and pre-incubated for 10 min. Substrate (10 μL) was added and the reaction proceeded in the dark at RT for 25 min. The final dilution of enzyme was 23 μg/ml, and the final concentration of substrate was 15 μM (Km of 25 μM). The fluorescence of the product was measured on a Victor II plate reader with an excitation wavelength of 360 nm and an emission wavelength of 485 nm using a protocol for labelled Edans peptide. The dimethyl sulfoxide control defined 100% activity level and 0% activity was defined by exclusion of the enzyme (using 40 mM MES pH 5.0 buffer instead).

TR-FRET Assay

Enzyme was diluted to 6 μg/mL and the substrate (Europium)CEVNLDAEFK(Qsy7) to 200 nM in reaction buffer (NaAcetate, chaps, triton x-100, EDTA pH 4.5). Compounds were diluted to the desired concentration in dimethyl sulfoxide (final dimethyl sulfoxide concentration in assay is 5%). The assay was done in a Costar 384 well round bottom, low volume, non-binding surface plate (Corning #3676). Enzyme (9 μL) and 1 μL of compound in dimethyl sulfoxide was added to the plate, mixed and pre-incubated for 10 min. Substrate (10 μL) was added and the reaction proceeded in the dark for 15 min at RT. The reaction was stopped with the addition of 7 μL NaAcetate, pH 9. The fluorescence of the product was measured on a Victor II plate reader with an excitation wavelength of 340 nm and an emission wavelength of 615 nm. The final concentration of the enzyme was 2.7 μg/ml and the final concentration of the substrate was 100 nM (Km of 290 nM). The dimethyl sulfoxide control defined the 100% activity level and 0% activity was defined by exclusion of the enzyme (using reaction buffer instead).

BACE Biacore Sensor Chip Preparation

BACE was assayed on a Biacore3000 instrument by attaching either a peptidic transition state isostere (TSI) or a scrambled version of the peptidic TSI to the surface of a Biacore CM5 sensor chip. The surface of a CM5 sensor chip has 4 distinct channels that can be used to couple the peptides. The scrambled peptide KFES-statine-ETIAEVENV was coupled to channel 1 and the TSI inhibitor KTEEISEVN-statine-VAEF was coupled to channel 2 of the same chip. The two peptides were dissolved at 0.2 mg/mL in 20 mM sodium acetate pH 4.5, and then the solutions were centrifuged at 14K rpm to remove any particulates. Carboxyl groups on the dextran layer were activated by injecting a one to one mixture of 0.5 M N-ethyl-N' (3-dimethylaminopropyl)-carbodiimide and 0.5 M N-hydroxysuccinimide at 5 μL/min for 7 min. Then the stock solution of the control peptide was injected in channel 1 for 7 min at 5 μL/min., and then the remaining activated carboxyl groups were blocked by injecting 1 M ethanolamine for 7 min at 5 μL/min.

BACE Biacore Assay Protocol

The BACE Biacore assay was done by diluting BACE to 0.5 μM in sodium acetate buffer at pH 4.5 (running buffer minus dimethyl sulfoxide). The diluted BACE was mixed with dimethyl sulfoxide or compound diluted in dimethyl sulfoxide at a final concentration of 5% dimethyl sulfoxide. The BACE/inhibitor mixture was incubated for 30 minutes at RT before being injected over channel 1 and 2 of the CM5 Biacore chip at a rate of 20 μL/min. As BACE bound to the chip the signal was measured in response units (RU). BACE binding to the TSI inhibitor on channel 2 gave a certain signal. The presence of a BACE inhibitor reduced the signal by binding to BACE and inhibiting the interaction with the peptidic TSI on the chip. Any binding to channel 1 was non-specific and was subtracted from the channel 2 responses. The dimethyl sulfoxide control was defined as 100% and the effect of the compound was reported as percent inhibition of the dimethyl sulfoxide control.

Beta-Secretase Whole Cell Assays

Generation of HEK293-APP695

The pcDNA3.1 plasmid encoding the cDNA of human full-length APP695 was stably transfected into HEK-293 cells using the Lipofectamine transfection reagent according to manufacture's protocol (Invitrogen). Colonies were selected with 0.1-0.5 mg/mL of zeocin. Limited dilution cloning was performed to generate homogeneous cell lines. Clones were characterized by levels of APP expression and Aβ secreted in the conditioned media using an ELISA assay developed in-house.

Cell culture for HEK293-APP695

HEK293 cells stably expressing human wild-type APP (HEK293-APP695) were grown at 37° C., 5% $CO_2$ in DMEM containing 4500 g/L glucose, GlutaMAX and sodium pyruvate supplemented with 10% FBS, 1% non-essential amino acids and 0.1 mg/mL of the selection antibiotic zeocin.

Aβ40 release assay

HEK293-APP695 cells were harvested at 80-90% confluence and seeded at a concentration of $0.2 \times 10^6$ cells/mL, 100 mL cell suspension/well, onto a black clear bottom 96-well poly-D-lysine coated plate. After over night incubation at 37° C., 5% $CO_2$, the cell medium was replaced with cell culture medium with penicillin and streptomycin (100 U/mL, 100 μg/mL, respectively) containing test compounds in a final dimethyl sulfoxide concentration of 1%. Cells were exposed to the test compounds for 24 h at 37° C., 5% $CO_2$. To quantify the amount of released Aβ, 100 μL cell medium was transferred to a round bottom polypropylene 96-well plate (assay plate). The cell plate was saved for the ATP assay, as described below. To the assay plate, 50 μL of primary detection solution containing 0.5 μg/mL of the rabbit anti-Aβ40 antibody and 0.5 μg/mL of the biotinylated monoclonal mouse 6E10 antibody in DPBS with 0.5%BSA and 0.5% Tween-20 was added per well and incubated over night at 4° C. Then, 50 μL of secondary detection solution containing 0.5 μg/mL of a ruthenylated goat anti-rabbit antibody and 0.2 mg/mL of streptavidin coated beads (Dynabeads M-280) was added per well. The plate was vigorously shaken at RT for 1-2 hours. The plate was then measured for electro-chemiluminescence in a BioVeris M8 Analyzer.

Cell culture for SH-SY5Y

SH-SY5Y cells were grown 37° C. with 5% $CO_2$ in DMEM/F-12 1:1 containing GlutaMAX supplemented with 1 mM HEPES, 10% FBS and 1% non-essential amino acids.

sAPPβ release assay

SH-SY5Y cells were harvested at 80-90% confluence and seeded at a concentration of $1.5 \times 10^6$ cells/mL, 100 mL cell suspension/well, onto a black clear flat bottom 96-well tissue culture plate. After 7 hours of incubation at 37° C., 5% $CO_2$, the cell medium was replaced with 90 μl cell culture medium with penicillin and streptomycin (100 U/mL, 100 μg/mL, respectively) containing test compounds in a final dimethyl sulfoxide concentration of 1%. Cells were exposed to the test compounds for 18 h at 37° C., 5% $CO_2$. To measure sAPPβ released into the cell medium, sAPPβ microplates from Meso Scale Discovery (MSD) were used and the assay was performed according to the manufacture's protocol.

Briefly, 25 μL cell medium was transferred to a previously blocked MSD sAPPβ microplate. The cell plate was saved for the ATP assay, as described below. The sAPPβ was captured during shaking at RT for 1hour, by antibodies spotted in the wells of the microplate. After multiple washes, SULFO-TAG labeled detection antibody was added (25 μL/well, final concentration 1 nM) to the assay plate and the plate was incubated with shaking at RT for 1 hour. Following multiple washes, 150 μl/well of Read Buffer T was added to the plate. After 10 minutes at RT the plate was read in the SECTOR™ Imager for electro-chemiluminescence.

ATP assay

As indicated above, after transferring medium for analysis of Aβ40 or sAPPβ from the cell plate, the plate was used to analyze cytotoxicity using the ViaLight™ Plus cell proliferation/cytotoxicity kit from Cambrex BioScience that measures total cellular ATP. The assay was performed according to the manufacture's protocol. Briefly, 50 μL cell lysis reagent was added per well. The plates were incubated at RT for 10 min. Two min after addition of 100 μL reconstituted ViaLight™ Plus ATP reagent, the luminescence was measured in a Wallac Victor² 1420 multilabel counter.

Results

Typical $K_i$ values for the compounds of the present invention are in the range of about 1 to about 100,000 nM. Biological data on exemplified final compounds is given below in Table III.

TABLE III

| Example No. | $K_i$ in TR-FRET assay |
|---|---|
| 5 | 282 nM |
| 6 | 275 nM |
| 7 | 178 nM |
| 8 | 339 nM |
| 9 | 295 nM |
| 10 | 324 nM |
| 11 | 219 nM |
| 12 | 398 nM |
| 16 | 91 nM |
| 17 | 62 nM |
| 21 | 93 nM |
| 22 | 170 nM |
| 23 | 88 nM |

The invention claimed is:

1. A compound according to Formula I

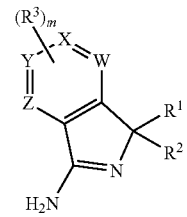

wherein
R¹ is selected from phenyl and pyridyl, wherein said phenyl or pyridyl is optionally substituted with one or more R⁴;
R² is selected from phenyl and pyridyl, wherein said phenyl or pyridyl is optionally substituted with one or more R⁴;
R³ is independently selected from halogen, $C_{1-6}$alkyl, $C_{2-6}$alkenyl, $C_{2-6}$alkynyl, wherein said $C_{1-6}$alkyl, $C_{2-6}$alkenyl, or $C_{2-6}$alkynyl, is optionally substituted with one or more R¹¹,
W is C;
X is C;
Y is C;
Z is N;
m is 0, 1, 2 or 3;
R⁴ is independently selected from halogen, $C_{0-6}$alkylOR⁵, $C_{1-6}$alkyl, $C_{2-6}$alkenyl, $C_{2-6}$alkynyl, phenyl, pyridyl and pyrimidyl, wherein said $C_{0-6}$alkylOR⁵, $C_{1-6}$alkyl, $C_{2-6}$alkenyl, $C_{2-6}$alkynyl, phenyl, pyridyl or pyrimidyl, is optionally substituted with one or more R¹¹,
R⁵ is selected from hydrogen, and $C_{1-6}$alkyl, wherein said $C_{1-6}$alkyl is optionally substituted with one or more A;
R⁸ is selected from hydrogen and $C_{1-6}$alkyl; wherein said $C_{1-6}$alkyl is optionally substituted with one or more A;
A is selected from oxo, and halogen;
R¹¹ is independently selected from halogen, $C_{0-6}$alkylOR⁸, $C_{1-6}$alkyl, $C_{2-6}$alkenyl, $C_{2-6}$alkynyl, wherein said $C_{1-6}$alkyl, $C_{2-6}$alkenyl, $C_{2-6}$alkynyl, is optionally substituted with one or more A;
as a free base or a pharmaceutically acceptable salt.

2. A compound according to claim 1, wherein m is 0.

3. A compound according to claim 1, wherein R¹ is phenyl, wherein said phenyl is optionally substituted with one R⁴.

4. A compound according to claim 3, wherein R¹ is phenyl, substituted with one R⁴.

5. A compound according to claim 1, wherein $R^4$ is selected from pyridyl and pyrimidyl wherein said pyridyl or pyrimidyl is optionally substituted with one or more $R^{11}$.

6. A compound according to claim 5, wherein $R^4$ is pyrimidyl.

7. A compound according to claim 5, wherein $R^4$ is pyridyl.

8. A compound according to claim 5, wherein $R^4$ is pyridyl, substituted with one $R^{11}$, said $R^{11}$ being halo.

9. A compound according to claim 5, wherein $R^4$ is pyridyl, substituted with one $R^{11}$, said $R^{11}$ being $C_{0-6}alkylOR^8$; wherein said $C_{0-6}alkylOR^8$ represents methoxy.

10. A compound according to claim 1, wherein $R^4$ is phenyl, wherein said phenyl is optionally substituted with one or more $R^{11}$.

11. A compound according to claim 10, wherein $R^4$ represents phenyl substituted with two $R^{11}$, said $R^{11}$ being one halo and one $C_{0-6}alkylOR^8$; wherein said $C_{0-6}alkylOR^8$ represents methoxy.

12. A compound according to claim 1, wherein $R^2$ is pyridyl.

13. A compound according to claim 1, wherein $R^2$ is phenyl substituted with one $R^{11}$.

14. A compound according to claim 13, wherein said $R^{11}$ represents $C_{0-6}alkylOR^8$; wherein said $C_{0-6}$ $alkylOR^8$ represents methoxy.

15. A compound according to Formula I

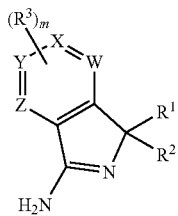

wherein
- $R^1$ is phenyl, wherein said phenyl is substituted with one $R^4$;
- $R^2$ is selected from phenyl and pyridyl, wherein said phenyl or pyridyl is optionally substituted with one $R^4$;
- W is C;
- X is C;
- Y is C;
- Z is N;
- m is 0;
- $R^4$ is independently selected from $C_{0-6}alkylOR^5$, phenyl, pyridyl and pyrimidyl, wherein said phenyl, pyridyl or pyrimidyl is optionally substituted with one or more $R^{11}$;
- $R^5$ is $C_{1-6}alkyl$;
- $R^8$ is $C_{1-6}alkyl$; and
- $R^{11}$ is independently selected from halogen and $C_{0-6}alkylOR^8$.

16. A compound selected from:
5-(4-Methoxyphenyl)-5-(3-pyrimidin-5-ylphenyl)-5H-pyrrolo[3,4-b]pyridin-7-amine;
5-[3-(2-Fluoropyridin-3-yl)phenyl]-5-(4-methoxyphenyl)-5H-pyrrolo[3,4-b]pyridin-7-amine;
5-(4-Methoxyphenyl)-5-[3-(5-methoxypyridin-3-yl)phenyl]-5H-pyrrolo[3,4-b]pyridin-7-amine;
5-(4-Methoxyphenyl)-5-(3-pyridin-3-ylphenyl)-5H-pyrrolo[3,4-b]pyridin-7-amine;
5-[3-(2-Fluoropyridin-3-yl)phenyl]-5-pyridin-4-yl-5H-pyrrolo[3,4-b]pyridin-7-amine;
5-Pyridin-4-yl-5-(3-pyrimidin-5-ylphenyl)-5H-pyrrolo[3,4-b]pyridin-7-amine;
5-(2'-Fluoro-5'-methoxybiphenyl-3-yl)-5-pyridin-4-yl-5H-pyrrolo[3,4-b]pyridin-7-amine 0.25 acetate;
5-(2'-Fluoro-3'-methoxybiphenyl-3-yl)-5-pyridin-4-yl-5H-pyrrolo[3,4-b]pyridin-7-amine 0.5 acetate;
3-Pyridin-4-yl-3-(3-pyrimidin-5-ylphenyl)-3H-pyrrolo[3,4-c]pyridin-1-amine;
3-[3-(2-Fluoropyridin-3-yl)phenyl]-3-pyridin-4-yl-3H-pyrrolo[3,4-c]pyridin-1-amine;
7-[3-(2-Fluoropyridin-3-yl)phenyl]-7-pyridin-4-yl-7H-pyrrolo[3,4-b]pyridin-5-amine;
7-Pyridin-4-yl-7-(3-pyrimidin-5-ylphenyl)-7H-pyrrolo[3,4-b]pyridin-5-amine; and
7-(2'-Fluoro-3'-methoxybiphenyl-3-yl)-7-pyridin-4-yl-7H-pyrrolo[3,4-b]pyridin-5-amine; as a free base or a pharmaceutically acceptable salt.

17. A pharmaceutical formulation comprising as active ingredient a therapeutically effective amount of a compound according to claim 1 in association with a pharmaceutically acceptable excipient, carrier or diluent.

18. A pharmaceutical formulation comprising as active ingredient a therapeutically effective amount of a compound according to claim 15 in association with a pharmaceutically acceptable excipient, carrier or diluent.

19. A pharmaceutical formulation comprising as active ingredient a therapeutically effective amount of a compound according to claim 16 in association with a pharmaceutically acceptable excipient, carrier or diluent.

* * * * *